United States Patent [19]
Sheppard et al.

[11] Patent Number: 6,084,088
[45] Date of Patent: Jul. 4, 2000

[54] POLYNUCLEOTIDES ENCODING NOVEL TUMOR ANTIGENS

[75] Inventors: Paul O. Sheppard, Redmond; Angelika Grossmann, Seattle, both of Wash.

[73] Assignee: ZymoGenetics, Inc., Seattle, Wash.

[21] Appl. No.: 09/073,569

[22] Filed: May 6, 1998

Related U.S. Application Data

[60] Provisional application No. 60/045,703, May 6, 1999.
[51] Int. Cl.$^7$ ...................................................... C07H 21/00
[52] U.S. Cl. ........................ 536/23.5; 435/69.1; 435/325; 435/91.1; 536/23.1; 536/24.1; 536/24.2; 530/350; 514/2
[58] Field of Search .................................. 435/69.1, 91.1, 435/325; 514/2, 12–19, 300–345, 350–385, 412; 536/23.1–24.2, 23.5; 530/350

[56] References Cited

PUBLICATIONS

Kerr et al, Analysis of cDNA sequences from mouse testis, Mamm, Genome 5(9): 557–565 (1994), Jun. 1994.

*Primary Examiner*—Julie Burke
*Assistant Examiner*—Larry R Helms
*Attorney, Agent, or Firm*—Deborah A. Sawislak

[57] ABSTRACT

The present invention relates to polynucleotide and polypeptide molecules for a secreted polypeptide designated zsig15. The polypeptides, and polynucleotides encoding them, may be used for mapping chromosome 19 and markers for tumor growth. The present invention also includes antibodies to the zsig15 polypeptides.

15 Claims, 10 Drawing Sheets

POLYNUCLEOTIDES ENCODING NOVEL TUMOR ANTIGENS

REFERENCE TO RELATED APPLICATIONS

This application is related to Provisional Application Ser. No. 60/045,703, filed on May 6, 1997. Under 35 U.S.C. §119(e)(1), this application claims benefit of said Provisional Application.

BACKGROUND OF THE INVENTION

Prostate, colon and breast tissues are all associated with a high prevalence of cancer, and are in fact with lung cancer, the most deadly forms of cancer in the United States today.

Prostate cancer is the most prevalent form of cancer in men in the United States. It is anticipated that an estimated 334,500 new cases of prostate cancer will be diagnosed in 1997 (in *Cancer Facts and Figures*: 1997, American Cancer Society, Atlanta, 1997). The incidence rate for prostate cancer has increased 50% between 1989 and 1993

Early diagnosis is critical for survival, for example, if a tumor is discovered while it is still localized, the 5 year survival rate is 99%. However, early diagnosis at the present time is limited to relatively unreliable methods. These methods include a digital rectal exam and prostate specific antigen (PSA) test. However, digital exam may require that the tumor has become quite large and the cancer may be at a more advanced stage. Ultrasonography has demonstrated that 20% to 30% of cancers detected using this method are not detectable using PSA tests. In addition, false positives are a significant problem as well (in *Cancer: Principles and Practice of Oncology*, DeVita, Hellman and Rosenberg (eds), J.B. Lippincott Company, Philadephia, pp:538–589, 1993).

Breast cancer is the second major cause of cancer death in women. Approximately 110/100,000 women will be diagnosed with breast cancer each year, and it is expected that in 1997 there will be 43,900 deaths related to breast cancer (in *Cancer Facts and Figures*: 1997, American Cancer Society, Atlanta, 1997). Early detection is the key to survival and mammograms are generally accepted as the most valuable tool that is available for early detection. Once a tumor is recognizable by physical symptoms the tumor has generally progressed.

An estimated 94,100 cases of colon cancer will be identified in 1997, and 10% of all cancer deaths will be related to colorectal cancer (in *Cancer Facts and Figures*: 1997, American Cancer Society, Atlanta, 1997). While diagnosis and treatment have been steadily improving, early detection is important for survival. In addition, the cells in these tissues have a high rate of turnover and metabolic activity, and therefore, generally produce a large spectrum of proteins. Included are proteins with secretory functions, and this is particularly common in tissue involved in transporting substances to the outside of the body. One type of substance produced by secretory tissues is anti-microbial agents, in particular antimicrobial proteins. These proteins can act via several mechanisms that include: enzymatic mechanisms, such as, breaking down microbial protective sustances or the microbial cell wall/membrane or the proteins can be very sticky and trap microorganisms. The antimicrobial proteins produced by secretory tissue play an important role in maintaining the body's ability to prevent infection in a more non-specific way than is generally associated with components of the immune system.

Thus, the present invention provides proteins that will be valuable as markers for changes in metabolism highly suspectible to cancerous growth, as well as other uses that should be apparent to those skilled in the art from the teachings herein.

SUMMARY OF THE INVENTION

The present invention provides an isolated polynucleotide molecule selected from the group consisting of: a) polynucleotide molecules comprising a nucleotide sequence as shown in SEQ ID NO: 1 from nucleotide 97 to nucleotide 1215; b) orthologs of (a); (c) allelic variants of (a) or (b); d) polynucleotide molecules that encode a polypeptide that is at least 80% identical to the amino acid sequence of SEQ ID NO: 2 from amino acid residue 22 (Leu) to amino acid residue 394 (Glu); and e) degenerate nucleotide sequences of (a), (b), (c) or (d).

In other embodiments, the polynucleotide molecule is selected from nucleotide sequences as shown in SEQ ID NO: 1 from nucleotides 97–1344, 79–1344, 34–1344, 97–582, 65–1215, or 65–1344; and the corresponding polynucleotide molecules that encode a polypeptide that is at least 80% identical to the amino acid sequence of SEQ ID NO: 2 from residues 22–437, 16–437, or 1–347, respectively.

In aspects, the present invention provides isolated polynucleotide molecules comprising a sequence of nucleotides from nucleotide 97–582, 655–1215, or 655–1344 of SEQ ID NO: 1.

In another aspect, the present invention provides a isolated polynucleotide molecule encoding a fusion protein comprising a first polypeptide and a second polypeptide, said first polypeptide encoded by a sequence of nucleotides as shown in SEQ ID NO: 1 from nucleotide 97 to nucleotide 582, and a second polypeptide encoded by a sequence of nucleotides as shown in SEQ ID NO: 1 from nucleotide 655 to nucleotide 1215.

In another aspect, the present invention provides an expression vector comprising the following operably linked elements: a transcription promoter; a DNA segment selected from the group consisting of: (a) polynucleotide molecules comprising a nucleotide sequence as shown in SEQ ID NO: 1 from nucleotide 97 to nucleotide 1215; (b) orthologs of (a); (c) allelic variants of (a) or (b); (d) polynucleotide molecules that encode a polypeptide that is at least 80% identical to the amino acid sequence of SEQ ID NO: 2 from amino acid residue 22 (Leu) to amino acid residue 394 (Glu); and (e) degenerate nucleotide sequences of (a), (b), (c) or (d); and a transcription terminator.

In another aspect, the present invention provides a cultured cell into which has been introduced an expression vector according as described above, wherein said cell expresses the polypeptide encoded by the DNA segment.

In another aspect, the present invention provides an isolated polypeptide selected from the group consisting of: (a) polypeptide molecules comprising an amino acid sequence as shown in SEQ ID NO: 2 from amino acid residue 22 (Leu) to amino acid residue 394 (Glu); (b) orthologs of (a); (c) allelic variants of (a) or (b); and (d) polypeptide molecules that are at least 80% identical to the amino acids of SEQ ID NO: 2 from amino acid residue 22 (Leu) to amino acid residue 394 (Glu).

In other embodiments, the present invention provides isolated polypeptides wherein said polypeptide molecules comprise an amino acid sequence as shown in SEQ ID NO: 2 from residues 22–437, 16–437 and 1–437.

In another aspect, the present invention provides isolated polypeptides comprising a sequence of amino acids as shown in SEQ ID NO: 2 from residue 22–183, 208–394 and 208–437.

In another aspect, the present invention provides an isolated fusion protein comprising a first polypeptide and a second polypeptide, said first polypeptide comprising a sequence of amino acid residues as shown in SEQ ID NO: 2 from residues 22–183, and a second polypeptide comprising a sequence amino acid residues as shown in SEQ ID NO: 2 from residues 208–394.

In another embodiment, the present invention provides an isolated polypeptide that is additionally covalently linked at the N-terminus or C-terminus to a moiety selected from the group consisting of affinity tags, toxins, radionucleotides, enzymes or fluorophores.

In another aspect, the present invention provides antibodies that specifically bind to an epitope of a polypeptide comprising a sequence of amino acids as shown in SEQ ID NO: 2 from residue 1–437.

In another aspect, the present invention provides a method of producing a polypeptide comprising: culturing a cell into which has been introduced an expression vector as described above, whereby said cell expresses a polypeptide encoded by the DNA segment; and recovering the polypeptide.

In another aspect, the present invention provides an oligonucleotide probe or primer comprising at least 14 contiguous nucleotides of polynucleotide of SEQ ID NO: 1 from nucleotide 34 to nucleotide 1344.

BRIEF DESCRIPTION OF THE DRAWINGS

FIGS. 1a–1j are Hopp/Woods hydrophilicity profile of the zsig15 protein sequence shown in SEQ ID NO:2. The profile is based on a sliding six-residue window. Buried G, S, and T residues and exposed H, Y, and W residues were ignored. These residues are indicated in the figure by lower case letters.

DETAILED DESCRIPTION OF THE INVENTION

Figure 1A:
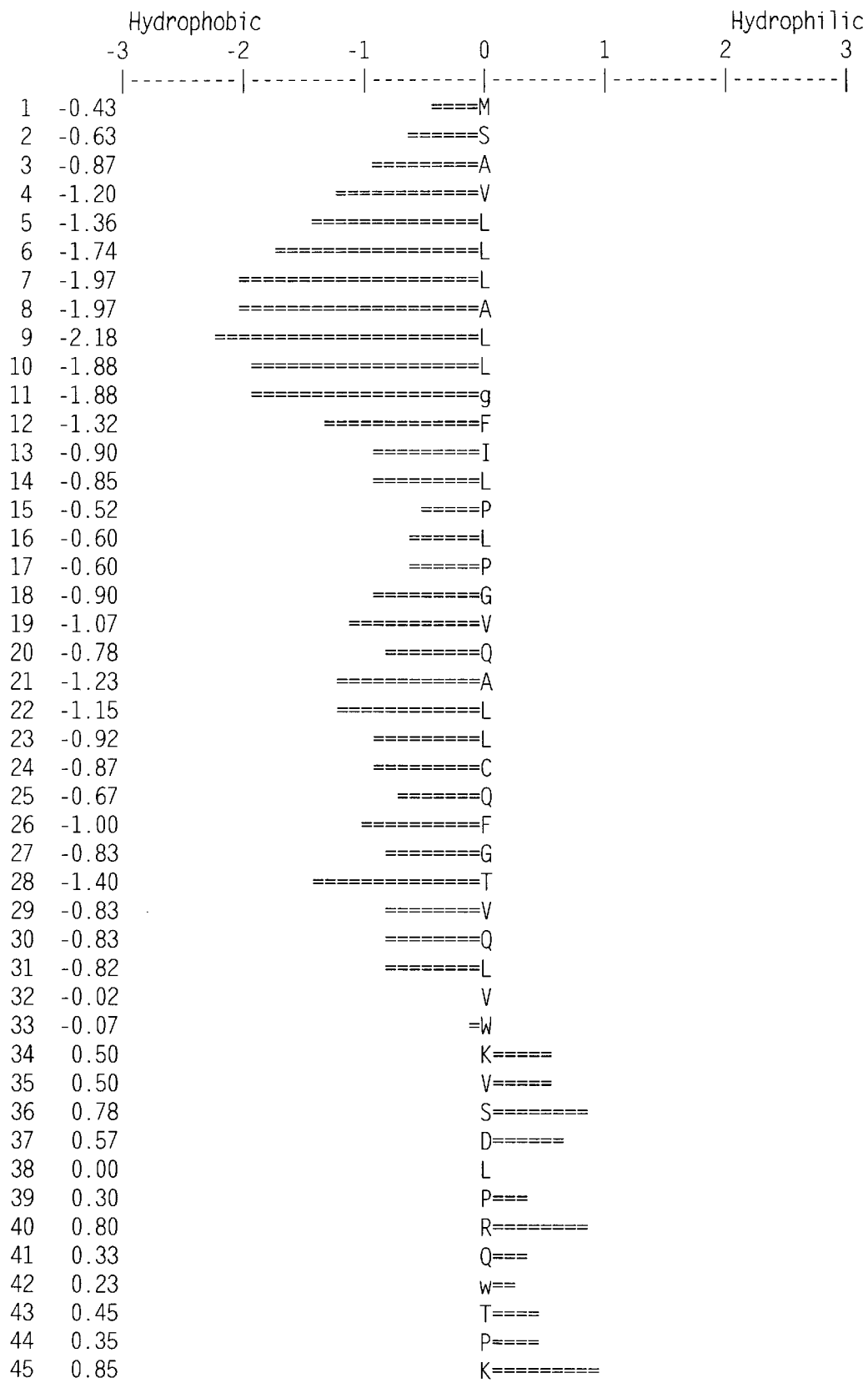

Prior to describing the present invention in detail, it may be helpful to define certain terms used herein:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952–4, 1985), substance P, Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" is a polynucleotide molecule having a complementary base sequence and reverse orientation as compared to a reference sequence.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e., greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. Most nuclear receptors also exhibit a multi-domain structure, including an amino-terminal, transactivating domain, a DNA binding domain and a ligand binding domain. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a componenet of a larger polypeptide directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNas transcribed from the same gene. Splice variants may encode polypeptides having latered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA sequence that encodes a secreted polypeptide. Analysis of the tissue distribution of the mRNA corresponding to this novel DNA revealed that expression was highest in prostate and bone marrow, followed by apparent but decreased expression levels in spinal cord, colon and pancreas. Transcripts of 1.7 and 2.5 kb in size were identified by northern analysis. The polypeptide has been designated zsig15. Northern blots of tumor and normal tissue further revealed mRNA expression in colon and breast at various stages of tumor development and/or normal tissue.

The novel zsig15 polypeptides of the present invention were initially identified by querying an EST database for sequences possessing a putative secretion signal. An EST sequence was discovered and was subsequently mapped to chromosome 19;q13.1–913.2. The EST sequence was originally derived from a colon tumor library.

The nucleotide sequence of zsig15 is described in SEQ ID NO. 1, and its deduced amino acid sequence is described in SEQ ID NO. 2. Analysis of the DNA encoding a zsig15 polypeptide (SEQ ID NO: 1) revealed an open reading frame encoding 437 amino acids (SEQ ID NO: 2) comprising a signal peptide of from 15 to 21 amino acid residues (residue 1 to residues 15 to 21 of SEQ ID NO: 2) and comprising a mature polypeptide of from 416 to 422 amino acids (residues 15–21 to residue 437 of SEQ ID NO: 2).

The polypeptide of the present invention contains at least 4 distinct regions. Two of these regions are direct repeats of each other. Starting from the mature peptide amino terminus (residue 16 or 22) region 1 is the first repeated domain as shown in SEQ ID NO: 2 from amino acid residue 22 (Leu) to residue 183 (Pro) and contains 12 Cysteine residues. Region 2 (residues 184 (Gly) to residue 207 (Asp) of SEQ ID NO: 2) appears to be a linker region and contains a pair of Cysteines. Region 3 (amino acid residue 208 (Phe) to residue 376 (Pro) of SEQ ID NO: 2) is the second repeated domain, and contains 12 Cysteines. Both repeated domains are predicted to be all beta-strand structure, which suggests a tertiary structure similarity with IG domains and cytokine receptor domains. The fourth domain is the C-terminus of the polypeptide (residues 377–437 of SEQ ID NO: 2) and contains a hydrophobic stretch which is a possible anchor for dimerization, membrane association, or hydrophobic matrix binding for the polypeptide, and contains a pair of Cysteines. The Arg-Lys, as shown in SEQ ID NO: 2 at residues 205–206 is a common processing site. Another putative processing site is found at residues 395–396 (Lys-Arg) of SEQ ID NO: 2. This cleavage site may serve to release the polypeptide as a free secretory component from the membrane-bound form of the protein and make it soluble. Generation of a free secretory component from a membrane-bound protein has been suggested for TNF-α (Rosendahl et al., *J. Biol. Chem.* 272(39):24588–24593, 1997).

The present invention provides polynucleotide molecules, including DNA and RNA molecules, that encode the zsig15 polypeptides disclosed herein. Those skilled in the art will readily recognize that, in view of the degeneracy of the genetic code, considerable sequence variation is possible among these polynucleotide molecules. SEQ ID NO:4 is a degenerate DNA sequence that encompasses all DNAs that encode the zsig15 polypeptide of SEQ ID NO:2. Those skilled in the art will recognize that the degenerate sequence of SEQ ID NO:4 also provides all RNA sequences encoding SEQ ID NO:2 by substituting U for T. Thus, zsig15 polypeptide-encoding polynucleotides comprising nucleotide 1 to nucleotide 1311 of SEQ ID NO:4 and their RNA equivalents are contemplated by the present invention. Table 1 sets forth the one-letter codes used within SEQ ID NO:4 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Nucleotide | Complement |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:4, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." In general, see, Grantham, et al., *Nuc. Acids Res.* 8:1893–912, 1980; Haas, et al. *Curr. Biol.* 6:315–24, 1996; Wain-Hobson, et al., *Gene* 13:355–64, 1981; Grosjean and Fiers, *Gene* 18:199–209, 1982; Holm, *Nuc. Acids Res.* 14:3075–87, 1986; Ikemura, *J. Mol. Biol.* 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:4 serves as a template for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NO:1, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

As previously noted, the isolated polynucleotides of the present invention include DNA and RNA. Methods for preparing DNA and RNA are well known in the art. In general, RNA is isolated from a tissue or cell that produces large amounts of zsig15 RNA. Such tissues and cells are identified by Northern blotting (Thomas, *Proc. Natl. Acad. Sci. USA* 77:5201, 1980), and include prostate, bone marrow, colon, breast and spinal cord. Total RNA can be prepared using guanidine HCl extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–12, 1972). Complementary DNA (cDNA) is prepared from poly(A)$^+$ RNA using known methods. In the alternative, genomic DNA can be isolated. Polynucleotides encoding zsig15 polypeptides are then identified and isolated by, for example, hybridization or PCR.

A full-length clone encoding zsig15 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to zsig15, receptor fragments, or other specific binding partners.

The present invention further provides counterpart polypeptides and polynucleotides from other species (orthologs). These species include, but are not limited to mammalian, avian, amphibian, reptile, fish, insect and other vertebrate and invertebrate species. Of particular interest are zsig15 polypeptides from other mammalian species, including murine, porcine, ovine, bovine, canine, feline, equine, and other primate polypeptides. orthologs of human zsig15 can be cloned using information and compositions provided by the present invention in combination with conventional cloning techniques. For example, a cDNA can be cloned using mRNA obtained from a tissue or cell type that expresses zsig15 as disclosed herein. Suitable sources of mRNA can be identified by probing Northern blots with probes designed from the sequences disclosed herein. A library is then prepared from mRNA of a positive tissue or cell line. A zsig15-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human zsig15 sequences disclosed herein. Within an additional method, the cDNA library can be used to transform or transfect host cells, and expression of the cDNA of interest can be detected with an antibody to zsig15 polypeptide. Similar techniques can also be applied to the isolation of genomic clones.

Those skilled in the art will recognize that the sequence disclosed in SEQ ID NO:1 represents a single allele of human zsig15 and that allelic variation and alternative splicing are expected to occur. Allelic variants can be cloned by probing cDNA or genomic libraries from different individuals according to standard procedures. Allelic variants of the DNA sequence shown in SEQ ID NO: 1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the zsig15 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The highly conserved amino acids in zsig15 can be used as a tool to identify new family members. For instance, reverse transcription-polymerase chain reaction (RT-PCR) can be used to amplify sequences encoding the conserved regions from RNA obtained from a variety of tissue sources or cell lines. In particular, highly degenerate primers designed from the zsig15 sequences are useful for this purpose.

The present invention also provides isolated zsig15 polypeptides that are substantially homologous to the polypeptides of SEQ ID NO:2 and their orthologs. The term "substantially homologous" is used herein to denote polypeptides having 60%, preferably 80%, more preferably at least 90, and most preferably at least 95%, sequence identity to the sequences shown in SEQ ID NO:2 or their orthologs. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes).

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The percent identity is then calculated as:

$$\frac{\text{Total number of identical matches}}{\text{[length of the longer sequence plus the number of gaps introduced into the longer sequence in order to align the two sequences]}} \times 100$$

Sequence identity of polynucleotide molecules is determined by similar methods using a ratio as disclosed above.

Variant zsig15 polypeptides or substantially homologous zsig15 polypeptides are characterized as having one or more amino acid substitutions, deletions or additions. These changes are preferably of a minor nature, that is conservative amino acid substitutions (see Table 4) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20–25 residues, or an affinity tag.

As described previously, the polypeptides of the present invention have at least 4 distinct regions. These regions (residues 22–183, residues 184–207, residues 208–376 and residues 377–437 of SEQ ID NO: 2) can be used independently or as fusion proteins in combination with other regions from polypeptides of the present invention or elsewhere. The present invention thus includes polypeptides of from 61 to 437 amino acid residues that comprise a sequence that is at least 80%, preferably at least 90%, and more preferably 95% or more identical to the corresponding region of SEQ ID NO:2. When combining polypeptides (or the polynucleotides that encode them), in one aspect of the present invention, the fusion protein comprises a first polypeptide and a second polypeptide, said first polypeptide comprises amino acid residues 22 (Leu) to 183 (Pro), or the polynucleotides encoding said polypeptide, and said second polypeptide comprises amino acid residues 208 (Phe) to 394 (Glu) or the polynucleotides encoding said polypeptide.

Polypeptides comprising covalently linked moieties, such as, affinity tags can further comprise a proteolytic cleavage site between the zsig15 polypeptide and the affinity tag. Preferred such sites include thrombin cleavage sites and factor Xa cleavage sites.

TABLE 4

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The present invention further provides a variety of other polypeptide fusions and related multimeric proteins comprising one or more polypeptide fusions. For example, a zsig15 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-zsig15 polypeptide fusions can be expressed in genetically engineered cells to produce a variety of multimeric zsig15 analogs. Auxiliary domains can be fused to zsig15 polypeptides to target them to specific cells, tissues, or macromolecules (e.g., collagen). For example, a zsig15 polypeptide or protein could be targeted to a predetermined cell type by fusing a zsig15 polypeptide to a ligand that specifically binds to a receptor on the surface of the target cell. In this way, polypeptides and proteins can be targeted for therapeutic or diagnostic purposes. A zsig15 polypeptide can be fused to two or more moieties, such as an affinity tag for purification and a targeting domain. Polypeptide fusions can also comprise one or more cleavage sites, particularly between domains. Fusion with moieties may be either at the N-terminus or C-terminus of the zsig15 polypeptide. See, Tuan et al., *Connective Tissue Research* 34:1–9, 1996.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an E. coli S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–809, 1993; and Chung et al., *Proc. Natl. Acad. Sci. USA* 90:10145–10149, 1993). In a second method, translation is carried out in Xenopus oocytes by microinjection of mutated mRNA and chemically aminoacylated suppressor tRNAs (Turcatti et al., *J. Biol. Chem.* 271:19991–19998, 1996). Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural amino acids may be substituted for zsig15 amino acid residues.

Essential amino acids in the polypeptides of the present invention can be identified according to procedures known in the art, such as site-directed mutagenesis or alanine-scanning mutagenesis (Cunningham and Wells, *Science* 244: 1081–1085, 1989; Bass et al., *Proc. Natl. Acad. Sci. USA* 88:4498–4502, 1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699–4708, 1996. Sites of ligand-receptor interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306–312, 1992; Smith et al., *J. Mol. Biol.* 224:899–904, 1992; Wlodaver et al., *FEBS Lett.* 309:59–64, 1992.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Figure 1B:
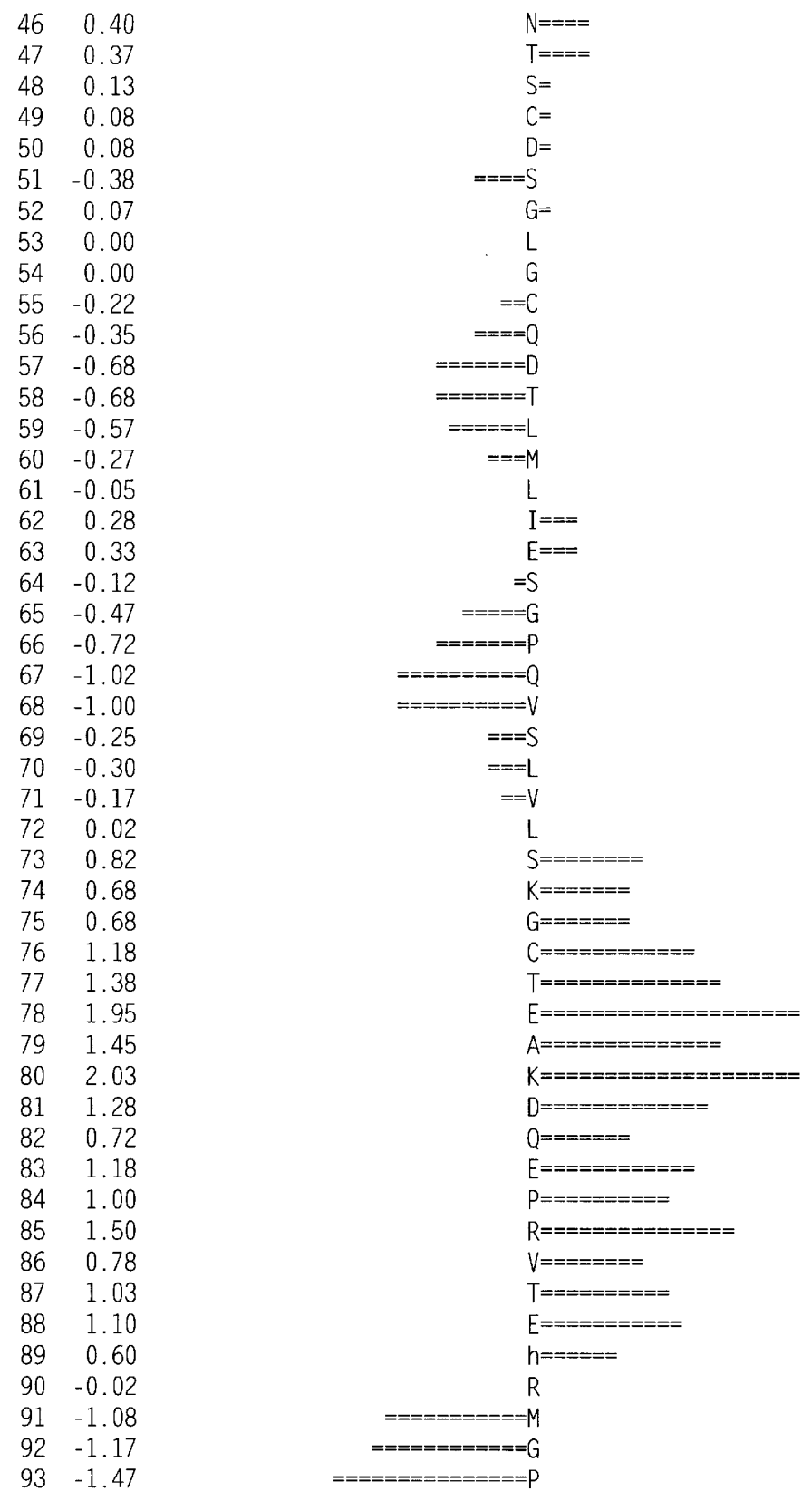
Figure 1C:
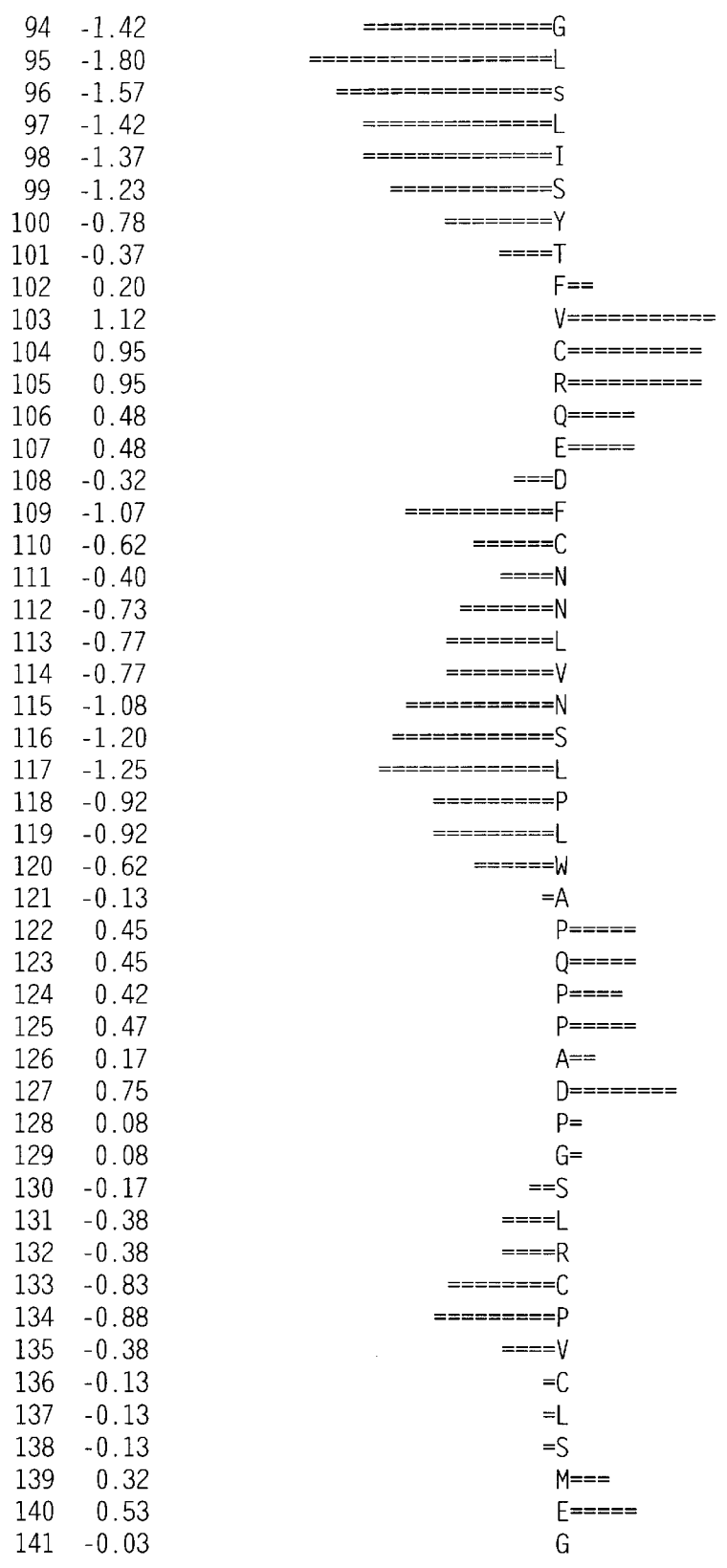
Figure 1D:
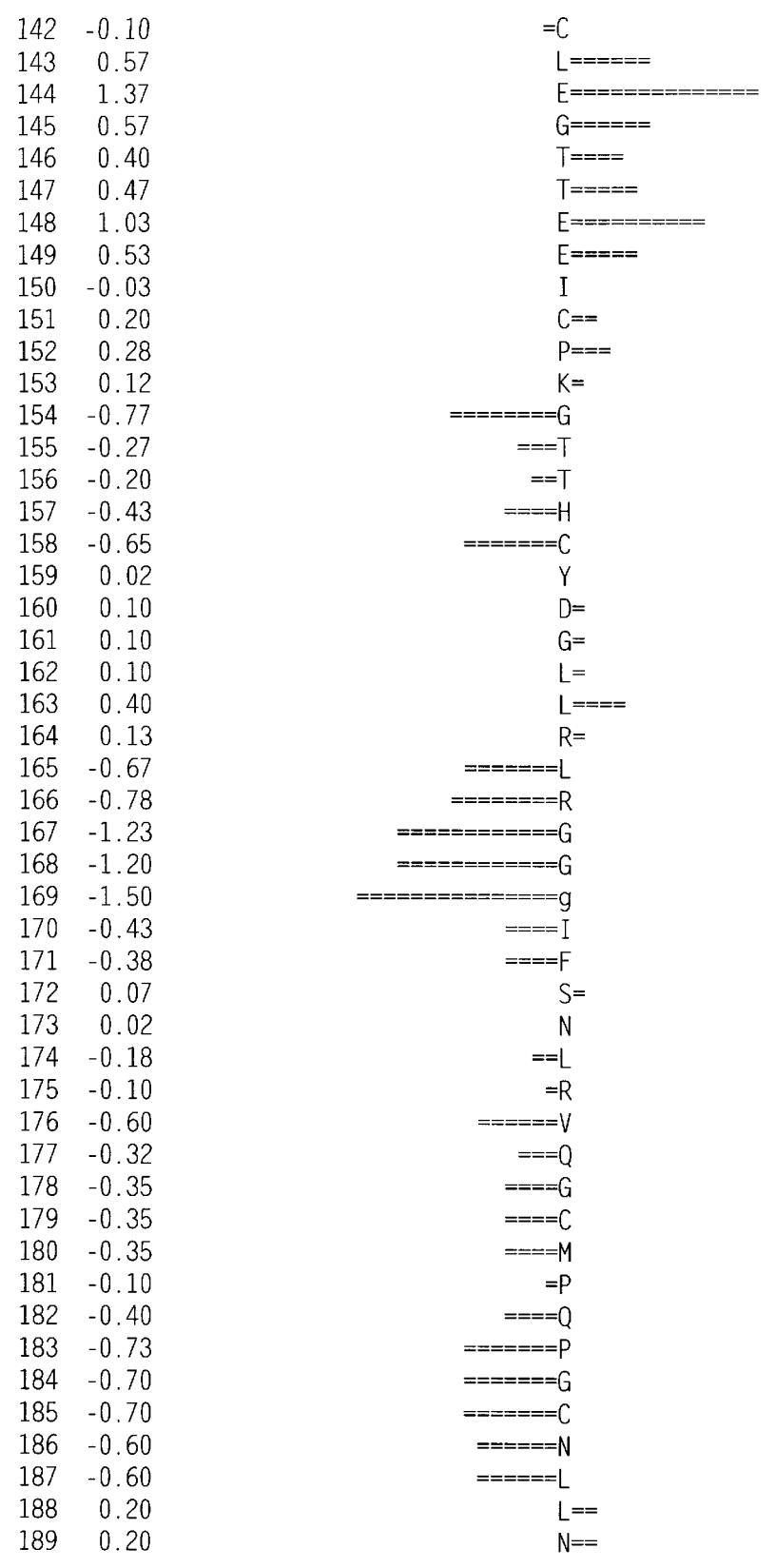
Figure 1E:
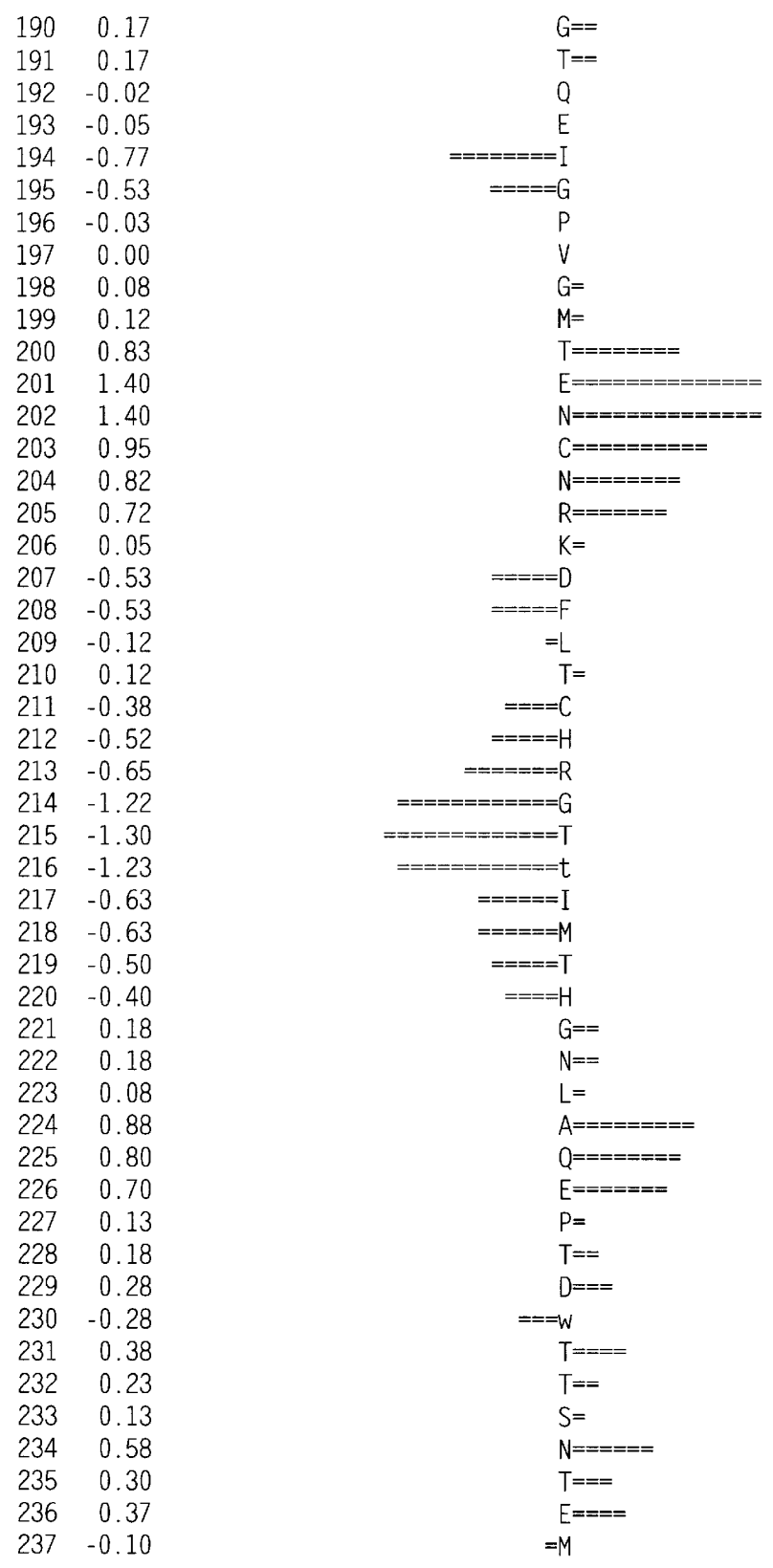
Figure 1F:
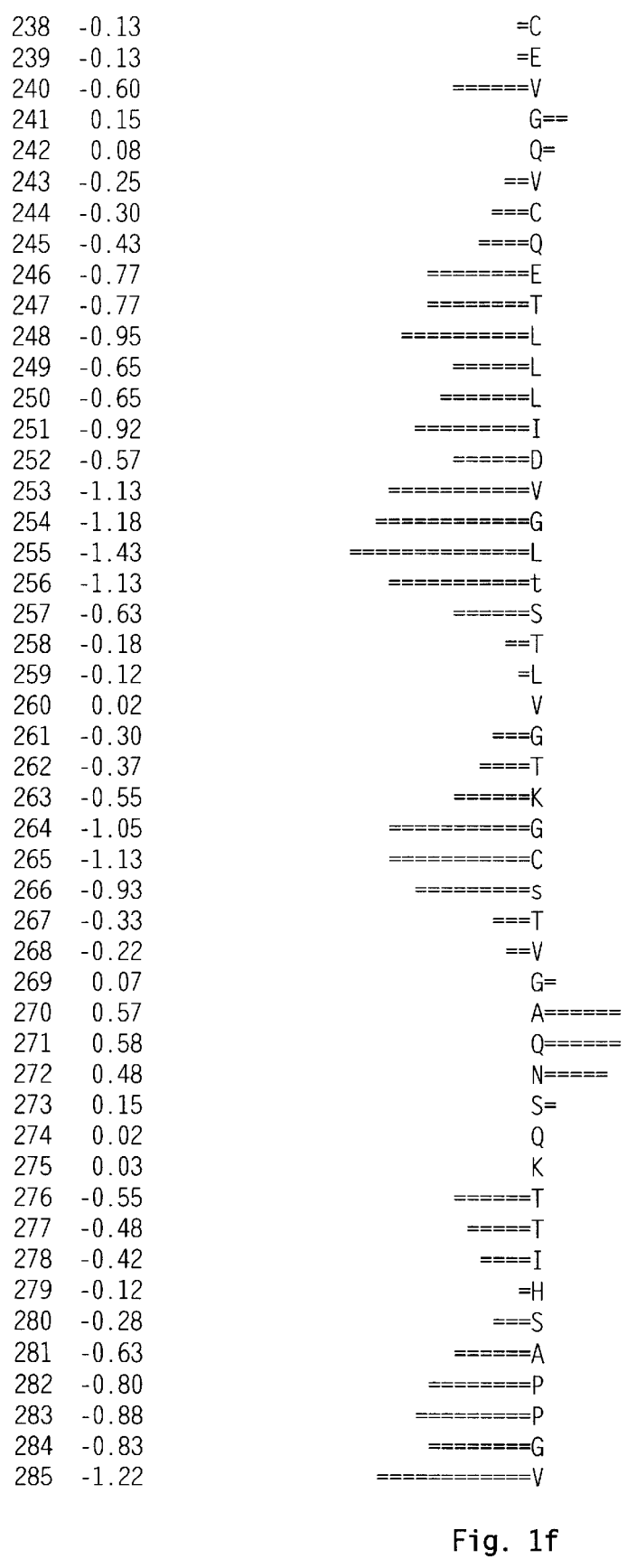
Figure 1G:
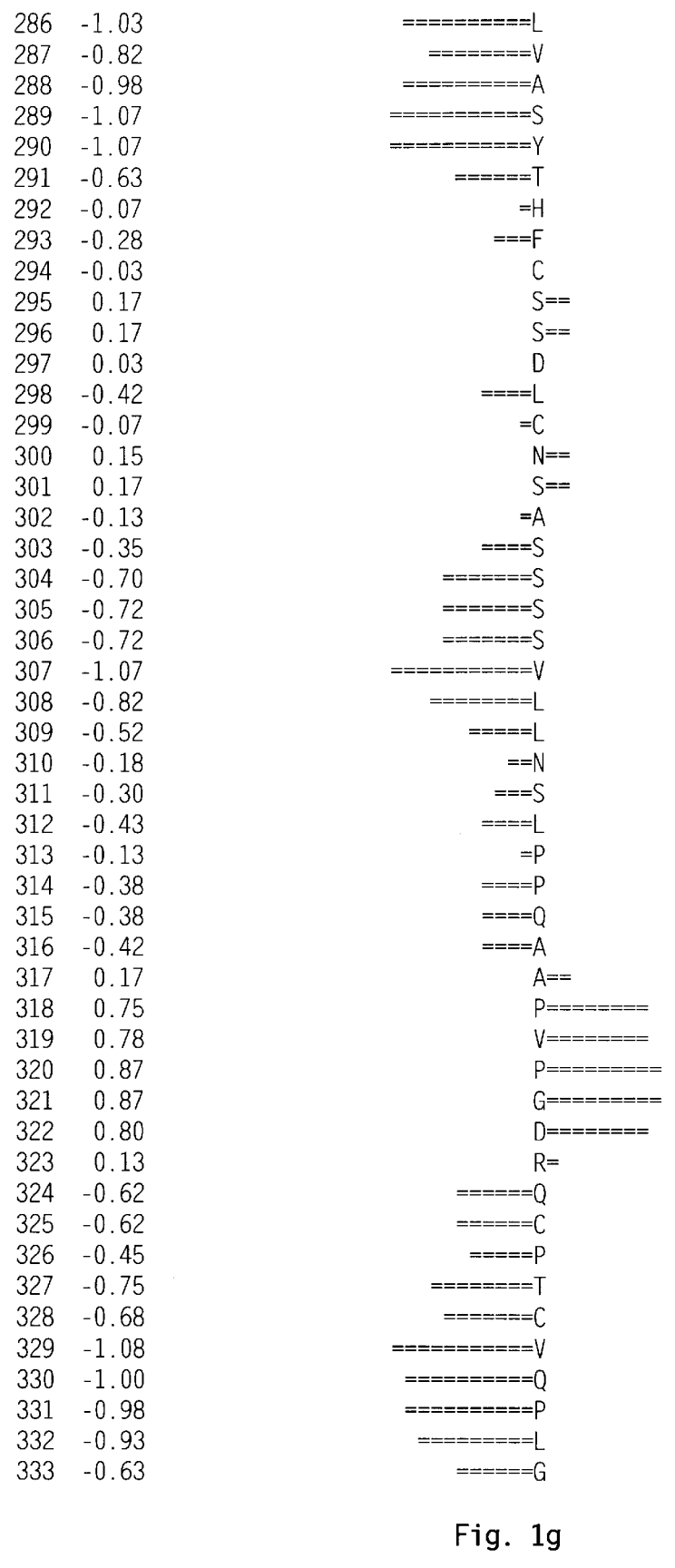
Figure 1H:
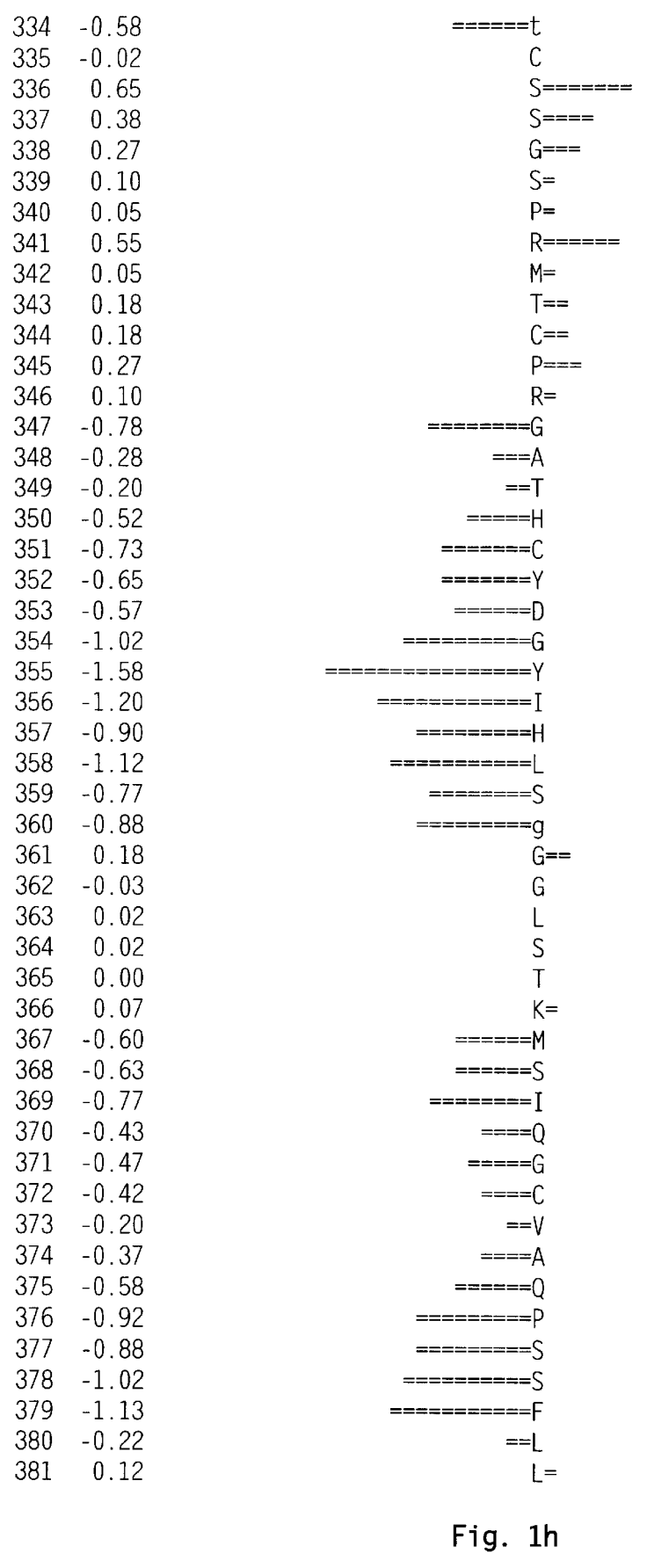
Figure 1I:
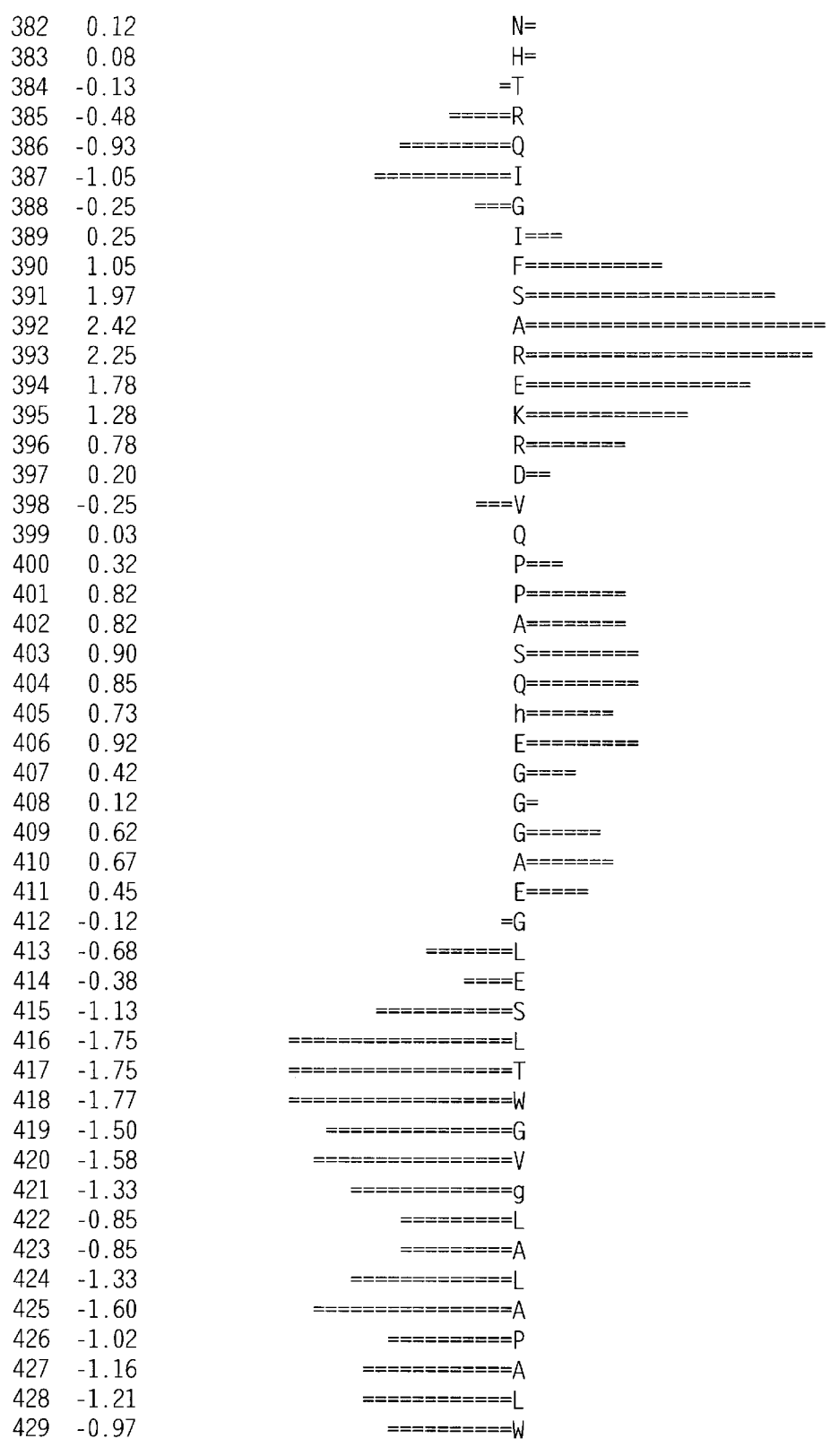
Figure 1J:
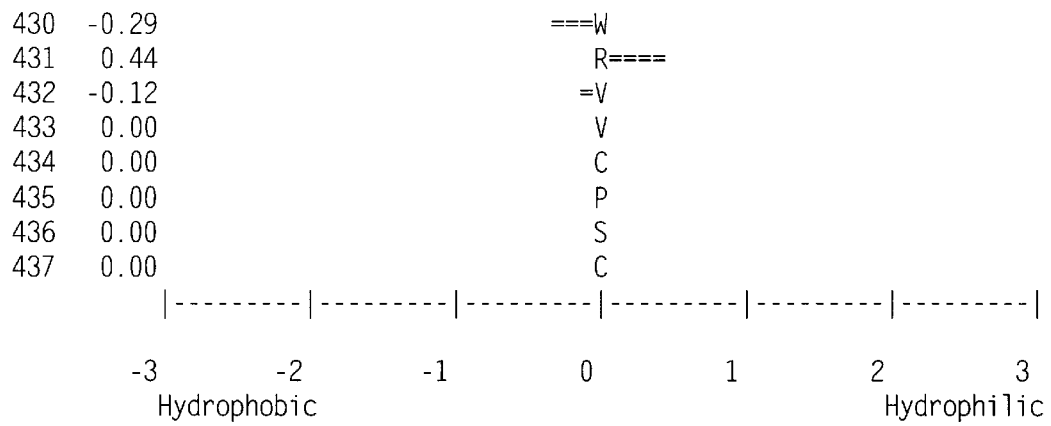

Amino acid sequence changes are made in zsig15 polypeptides so as to minimize disruption of higher order structure essential to biological activity. In this regard, it is generally preferred to retain the overall hydrophilicity profile of the natural sequence. A hydrophilicity profile of the sequence shown in SEQ ID NO:2 is shown in FIG. 1.

Variants of the disclosed zsig15 DNA and polypeptide sequences can be generated through DNA shuffling as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed herein, one of ordinary skill in the art can identify and/or prepare a variety of polypeptide fragments or variants of SEQ ID NO:2 or that retain the properties of the wild-type zsig15 protein.

The zsig15 polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., New York, 1987.

In general, a DNA sequence encoding a zsig15 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zsig15 polypeptide into the secretory pathway of a host cell, a secretory signal sequence (also known as a leader sequence, prepro sequence or pre sequence) is provided in the expression vector. The secretory signal sequence may be that of zsig15, or may be derived from another secreted protein (e.g., t-PA) or synthesized de novo. The secretory signal sequence is operably linked to the zsig15 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. A signal fusion polypeptide can be made wherein a secretory signal sequence derived from amino acid residues 1 to 15 through 21 of SEQ ID NO:2 is be operably linked to another polypeptide using methods known in the art and disclosed herein. The secretory signal sequence contained in the fusion polypeptides of the present invention is preferably fused aminoterminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993), and viral vectors (Miller and Rosman, *BioTechniques* 7:980–90, 1989; Wang and Finer, *Nature Med.* 2:714–716, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bancalore)* 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). DNA encoding the zsig15 polypeptide is inserted into the baculoviral genome in place of the AcNPV polyhedrin gene coding sequence by one of two methods. The first is the traditional method of homologous DNA recombination between wild-type AcNPV and a transfer vector containing the zsig15 flanked by AcNPV sequences. Suitable insect cells, e.g. SF9 cells, are infected with wild-type AcNPV and transfected with a transfer vector comprising a zsig15 polynucleotide operably linked to an AcNPV polyhedrin gene promoter, terminator, and flanking sequences. See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. Natural recombination within an insect cell will result in a recombinant baculovirus which contains zsig15 driven by the polyhedrin promoter. Recombinant viral stocks are made by methods commonly used in the art.

The second method of making recombinant baculovirus utilizes a transposon-based system described by Luckow (Luckow, V. A, et al., *J Virol* 67:4566–79, 1993). This system is sold in the Bac-to-Bac kit (Life Technologies, Rockville, Md.). This system utilizes a transfer vector, pFastBac1™ (Life Technologies) containing a Tn7 transposon to move the DNA encoding the zsig15 polypeptide into a baculovirus genome maintained in *E. coli* as a large plasmid called a "bacmid." The pFastBac1™ transfer vector utilizes the AcNPV polyhedrin promoter to drive the expression of the gene of interest, in this case zsig15. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins, M. S. and Possee, R. D., *J Gen Virol* 71:971–6, 1990; Bonning, B. C. et al., *J Gen Virol* 75:1551–6, 1994; and, Chazenbalk, G. D., and Rapoport, B., *J Biol Chem* 270:1543–9, 1995. In such transfer vector constructs, a short or long version of the basic protein promoter can be used. Moreover, transfer vectors can be constructed which replace the native zsig15 secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native zsig15 secretory signal sequence. In addition, transfer vectors can include an in-frame fusion with DNA encoding an epitope tag at the C- or N-terminus of the expressed zsig15 polypeptide, for example, a Glu-Glu epitope tag (Grussenmeyer, T. et al., *Proc Natl Acad Sci.* 82:7952–4, 1985). Using a technique known in the art, a transfer vector containing zsig15 is transformed into *E. Coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zsig15 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and ExcellO405™ (JRH Biosciences, Lenexa, Kans.) or Express FiveO™ (Life Technologies) for the *T. ni* cells. The cells are grown up from an inoculation density of approximately $2-5 \times 10^5$ cells to a density of $1-2 \times 10^6$ cells at which time a recombinant viral stock is added at a multiplicity of infection (MOI) of 0.1 to 10, more typically near 3. The recombinant virus-infected cells typically produce the recombinant zsig15 polypeptide at 12–72 hours post-infection and secrete it with varying efficiency into the medium. The culture is usually harvested 48 hours post-infection. Centrifugation is used to separate the cells from the medium (supernatant). The supernatant containing the zsig15 polypeptide is filtered through micropore filters, usually 0.45 µm pore size. Procedures used are generally described in available laboratory manuals (King, L. A. and Possee, R. D., ibid.; O'Reilly, D. R. et al., ibid.; Richardson, C. D., ibid.). Subsequent purification of the zsig15 polypeptide from the supernatant can be achieved using methods described herein.

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (τ) of from 1 to 40 milliseconds, most preferably about 20 milliseconds.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a zsig15 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

*P. methanolica* cells are cultured in a medium comprising adequate sources of carbon, nitrogen, and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

zsig15 polypeptides or fragments thereof may also be prepared through chemical synthesis. zsig15 polypeptides may be monomers or multimers; glycosylated or non-glycosylated; pegylated or non-pegylated; and may or may not include an initial methionine amino acid residue.

Polypeptides of the present invention are useful for measuring changes in levels of expression zsig15 polypeptides. Because zsig15 expression is restricted to specific tissues (i.e., prostate, colon and breast) and bone marrow, changes in expression levels could be used to monitor metabolism within these tissues. For example, increases in expression and/or transcription of zsig15 polypeptides and polynucleotides, may be predictive for increased cell proliferation of tumor cells. Furthermore, expression of zsig15 in tissue not normally expressing zsig15, may be indicative of metastases of tumor cells.

Zsig15 has been demonstrated to be expressed differentially in certain epithelial tissues and carcinomas, particularly in colon and breast. Differential expression is the transient expression, or lack thereof, of specific genes, proteins or other phenotypic properties (known as differentiation markers) that occur during the progress of maturation in a cell or tissue. A set of differentiation markers is defined as one or more phenotypic properties that can be identified and are specific to a particular cell type. Thus, pluripotent stem cells that can regenerate without commitment to a lineage express a set of differentiation markers that are lost when commitment to a cell lineage is made. Precursor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products and receptors.

Zsig15 expression can be used as a differentiation marker in normal and tumor tissues to determine the stage of the tumor or maturity of a cell. Zsig15 will be particularly valuable as a marker for epithelial cells and tumor of epithelial origin, and more particularly epithelial cells and epithelial-derived tumors from colon, breast or prostate tissues.

A set of differentiation markers is defined as one or more phenotypic properties that can be identified and are specific to a particular cell type. Differentiation markers are transiently exhibited at various stages of cell lineage. Pluripotent stem cells that can regenerate without commitment to a lineage express a set of differentiation markers that are lost when commitment to a cell lineage is made. Precursor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products and receptors.

The activity of molecules of the present invention can be measured using a variety of assays that measure proliferation and/or differentiation of specific cell types, chemotaxis, adhesion, changes in ion channel influx, regulation of second messenger levels and neurotransmitter release. Such assays are well known in the art. See, for example, in "Basic & Clinical Endocrinology Ser., Vol. Vol. 3," *Cytochemical Bioassays: Techniques & Applications*, Chayen; Chayen, Bitensky, eds., Dekker, New York, 1983.

Proliferation and differentiation can be measured using cultured cells or in vivo by administering molecules of the claimed invention to the appropriate animal model. Assays measuring cell proliferation or differentiation are well known in the art. For example, assays measuring proliferation include such assays as chemosensitivity to neutral red dye (Cavanaugh et al., *Investigational New Drugs* 8:347–354, 1990, incorporated herein by reference), incorporation of radiolabelled nucleotides (Cook et al., *Analytical Biochem*. 179:1–7, 1989, incorporated herein by reference), incorporation of 5-bromo-2'-deoxyuridine (BrdU) in the DNA of proliferating cells (Porstmann et al., *J. Immunol. Methods* 82:169–179, 1985, incorporated herein by reference), and use of tetrazolium salts (Mosmann, *J. Immunol. Methods* 65:55–63, 1983; Alley et al., *Cancer Res*. 48:589–601, 1988; Marshall et al., *Growth Reg*. 5:69–84, 1995; and Scudiero et al., *Cancer Res*. 48:4827–4833, 1988; all incorporated herein by reference). Assays measuring differentiation include, for example, measuring cell-surface markers associated with stage-specific expression of a tissue, enzymatic activity, functional activity or morphological changes (Watt, *FASEB*, 5:281–284, 1991; Francis, *Differentiation* 57:63–75, 1994; Raes, *Adv. Anim. Cell Biol. Technol. Bioprocesses*, 161–171, 1989; all incorporated herein by reference).

Polypeptides of the present invention can be measured in vitro using cultured cells or in vivo by administering molecules of the claimed invention to the appropriate animal model. For instance, BHK transfected expression host cells may be embedded in an alginate environment and injected (implanted) into recipient animals. Alginate-poly-L-lysine microencapsulation, permselective membrane encapsulation and diffusion chambers have been described as a means to entrap transfected mammalian cells or primary mammalian cells. These types of non-immunogenic "encapsulations" or microenvironments permit the transfer of nutrients into the microenvironment, and also permit the diffusion of proteins and other macromolecules secreted or released by the captured cells across the environmental barrier to the recipient animal. Most importantly, the capsules or microenvironments mask and shield the foreign, embedded cells from the recipient animal's immune response. Such microenvironments can extend the life of the injected cells from a few hours or days (naked cells) to several weeks (embedded cells).

Alginate threads provide a simple and quick means for generating embedded cells. The materials needed to generate the alginate threads are readily available and relatively inexpensive. Once made, the alginate threads are relatively strong and durable, both in vitro and, based on data obtained using the threads, in vivo. The alginate threads are easily manipulable and the methodology is scalable for preparation of numerous threads. In an exemplary procedure, 3% alginate is prepared in sterile $H_2O$, and sterile filtered. Just prior to preparation of alginate threads, the alginate solution is again filtered. An approximately 50% cell suspension (containing about $5 \times 10^5$ to about $5 \times 10^7$ cells/ml) is mixed with the 3% alginate solution. One ml of the alginate/cell suspension is extruded into a 100 mM sterile filtered $CaCl_2$ solution over a time period of ~15 min, forming a "thread". The extruded thread is then transferred into a solution of 50 mM $CaCl_2$, and then into a solution of 25 mM $CaCl_2$. The thread is then rinsed with deionized water before coating the thread by incubating in a 0.01% solution of poly-L-lysine. Finally, the thread is rinsed with Lactated Ringer's Solution and drawn from solution into a syringe barrel (without needle attached). A large bore needle is then attached to the syringe, and the thread is intraperitoneally injected into a recipient in a minimal volume of the Lactated Ringer's Solution.

An alternative in vivo approach for assaying proteins of the present invention involves viral delivery systems. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see T. C. Becker et al., *Meth. Cell Biol.* 43:161–89, 1994; and J. T. Douglas and D. T. Curiel, *Science & Medicine* 4:44–53, 1997). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293S cells can be grown in suspension culture at relatively high cell density to produce significant amounts of protein (see Garnier et al., *Cytotechnol.* 15:145–55, 1994). With either protocol, an expressed, secreted heterologous protein can be repeatedly isolated from the cell culture supernatant. Within the infected 293S cell production protocol, non-secreted proteins may also be effectively obtained.

Expressed recombinant zsig15 polypeptides (or chimeric zsig15 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of specific properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp.529–39). Within additional embodiments of the invention, a fusion of the polypeptide of interest and an affinity tag (e.g., maltose-binding protein, an immunoglobulin domain) may be constructed to facilitate purification.

Using methods described in the art, polypeptide fusions, or hybrid zsig15 proteins, are constructed using regions or domains of the inventive zsig15 in combination with those of other heterologous proteins (Sambrook et al., ibid., Altschul et al., ibid., Picard, *Cur. Opin. Biology*, 5:511–5, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a domain(s) conferring a biological function may be swapped between zsig15 of the present invention with the functionally equivalent domain(s) from another family member. Such domains include, but are not limited to, the secretory signal sequence and conserved motifs. Such fusion proteins would be expected to have a biological functional profile that is the same or similar to polypeptides of the present invention or other family, depending on the fusion constructed. Moreover, such fusion proteins may exhibit other properties as disclosed herein.

The gene for molecules of the present invention has been mapped to the chromosomal location 19Q 13.1–13.2. This chromosomal location is distinguished by a clustering of multiple genes, that when expressed at high level, are associated with carcinomas. Kallikrein/Prostate-specific antigen (PSA) is localized to chromosome 19Q 13.12–13.4 and has been shown to be overexpressed in prostate cancers (Winderickx et al., *Mol. Cell. Endocrinol.* 62:217–226, 1989). PSA is a single chain glycoprotein of 33 kDa. Another cluster of genes localized to chromosome 19Q 13.1–13.3 is the pregnancy-specific beta glycoprotein family (PSBGs). PSBGs have been used to diagnose pregnancy, hydatidiform moles and choriocarcinoma (McLenachan et al., *Genomics* 22:356–363, 1994). The PSBGs are members of the immunoglobin super family and related to another gene family found in this cluster, carcinoembryonic antigen (CEA). CEA gene family is located on the long arm of chromosome 19 and has been identified as a marker for colorectal, gastric and pancreatic carcinomas (Hodge, *Cancer Immunol. Immunother.* 43:127–143, 1996). Thus, the gene of the present invention provides an additional tool for further elucidation of a chromosomal location that is believed to be important in diagnosis of various cancers.

In addition, family studies can be done to identify whether the gene for zsig15 is mutated and therefore indicative of an inherited form of disease. Mutations of genes can identified by methods well known to those with ordinary skill in such arts. For example, nucleic acids (i.e., genomic DNA, cDNA or mRNA) are extracted from tissue samples or biological fluids and analyzed by PCR using PCR primers complementary to nucleic acids of the present invention. Analyses involve identification of insertions, deletions and substitutions that may, for example, differ in mobility when subjected to gel electrophorsis or can be cleaved by ribonuclease at single base mismatch in a RNA-DNA heteroduplex (Myers et al., *Science*, 230:1242–1246, 1985).

zsig15 polypeptides can also be used to prepare antibodies that specifically bind to zsig15 epitopes, peptides or polypeptides. Methods for preparing polyclonal and monoclonal antibodies are well known in the art.

In view of the tissue distribution observed for zsig15, agonists (including the natural ligand/substrate/cofactor/ etc.) and antagonists have potential in both in vitro and in vivo applications. For example, zsig15 and agonist compounds are useful as components of defined cell culture media, and may be used alone or in combination with other cytokines and hormones to replace serum that is commonly used in cell culture. Agonists are thus useful in specifically promoting the growth and/or development of epithelial cells, particularly of colon or breast tissue origin.

Antagonists are also useful as research reagents for characterizing sites of ligand-receptor interaction. Inhibitors of zsig15 activity (zsig15 antagonists) include anti-zsig15 antibodies and soluble zsig15 receptors, as well as other peptidic and non-peptidic agents (including ribozymes).

zsig15 can also be used to identify inhibitors (antagonists) of its activity. Test compounds are added to the assays disclosed herein to identify compounds that inhibit the activity of zsig15. In addition to those assays disclosed herein, samples can be tested for inhibition of zsig15 activity within a variety of assays designed to measure receptor binding or the stimulation/inhibition of zsig15-dependent cellular responses. For example, zsig15-responsive cell lines can be transfected with a reporter gene construct that is responsive to a zsig15-stimulated cellular pathway. Reporter gene constructs of this type are known in the art, and will generally comprise a zsig15-DNA response element operably linked to a gene encoding an assayable protein, such as luciferase. DNA response elements can include, but are not limited to, cyclic AMP response elements (CRE), hormone response elements (HRE) insulin response element (IRE) (Nasrin et al., *Proc. Natl. Acad. Sci. USA* 87:5273–7, 1990) and serum response elements (SRE) (Shaw et al. *Cell* 56: 563–72, 1989). Cyclic AMP response elements are reviewed in Roestler et al., *J. Biol. Chem.* 263 (19):9063–6; 1988 and Habener, *Molec. Endocrinol.* 4 (8):1087–94; 1990. Hormone response elements are reviewed in Beato, *Cell* 56:335–44; 1989. Candidate compounds, solutions, mixtures or extracts are tested for the ability to inhibit the activity of zsig15 on the target cells as evidenced by a decrease in zsig15 stimulation of reporter gene expression. Assays of this type will detect compounds that directly block zsig15 binding to cell-surface receptors, as well as compounds that block processes in the cellular pathway subsequent to receptor-ligand binding. In the alternative, compounds or other samples can be tested for direct blocking of zsig15 binding to receptor using zsig15 tagged with a detectable label (e.g., $^{125}$I, biotin, horseradish peroxidase, FITC, and the like). Within assays of this type, the ability of a test sample to inhibit the binding of labeled zsig15 to the receptor is indicative of inhibitory activity, which can be confirmed through secondary assays. Receptors used within binding assays may be cellular receptors or isolated, immobilized receptors.

A zsig15 polypeptide, or portions thereof, can be expressed as a fusion with an immunoglobulin heavy chain constant region, typically an $F_c$ fragment, which contains two constant region domains and lacks the variable region. Methods for preparing such fusions are disclosed in U.S. Pat. Nos. 5,155,027 and 5,567,584. Such fusions are typically secreted as multimeric molecules wherein the Fc portions are disulfide bonded to each other and two non-Ig polypeptides are arrayed in closed proximity to each other. Fusions of this type can be used to affinity purify ligand, as in vitro assay tool, or antagonist. For use in assays, the chimeras are bound to a support via the $F_c$ region and used in an ELISA format.

A zsig15 ligand-binding polypeptide can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–48, 1991; Cunningham et al., *Science* 245:821–25, 1991).

zsig15 polypeptides can also be used to prepare antibodies that specifically bind to zsig15 epitopes, peptides or polypeptides. The zsig15 polypeptide or a fragment thereof serves as an antigen (immunogen) to inoculate an animal and elicit an immune response. Antibodies generated from this immune response can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals, such as horses, cows, goats, sheep, dogs, chickens, rabbits, mice, and rats with a zsig15 polypeptide or a fragment thereof. The immunogenicity of a zsig15 polypeptide may be increased through the use of an adjuvant, such as alum (aluminum hydroxide) or Freund's complete or incomplete adjuvant. Polypeptides useful for immunization also include fusion polypeptides, such as fusions of zsig15 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to zsig15 protein or peptide, and selection of antibody display libraries in phage or similar vectors (for instance, through use of immobilized or labeled zsig15 protein or peptide). Genes encoding polypeptides having potential zsig15 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the zsig15 sequences disclosed herein to identify proteins which bind to zsig15. These "binding proteins" which interact with zsig15 polypeptides can be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as zsig15 "antagonists" to block zsig15 binding and signal transduction in vitro and in vivo. These anti-zsig15 binding proteins would be useful for inhibiting ???.

Antibodies are determined to be specifically binding if: 1) they exhibit a threshold level of binding activity, and/or 2) they do not significantly cross-react with related polypeptide molecules. First, antibodies herein specifically bind if they bind to a zsig15 polypeptide, peptide or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., *Ann. NY Acad. Sci.* 51: 660–672, 1949).

Second, antibodies are determined to specifically bind if they do not significantly cross-react with related polypeptides. Antibodies do not significantly cross-react with related polypeptide molecules, for example, if they detect zsig15 but not known related polypeptides using a standard Western blot analysis (Ausubel et al., ibid.). Examples of known related polypeptides are orthologs, proteins from the same species that are members of a protein family (e.g. IL-16), zsig15 polypeptides, and non-human zsig15. Moreover, antibodies may be "screened against" known related polypeptides to isolate a population that specifically binds to the inventive polypeptides. For example, antibodies raised to zsig15 are adsorbed to related polypeptides adhered to insoluble matrix; antibodies specific to zsig15 will flow through the matrix under the proper buffer conditions. Such screening allows isolation of polyclonal and monoclonal antibodies non-crossreactive to closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., Adv. in Immunol. 43: 1–98, 1988; *Monoclonal Antibodies: Principles and Practice*, Goding, J. W. (eds.), Academic Press Ltd., 1996; Benjamin et al., *Ann. Rev. Immunol.* 2: 67–101, 1984.

A variety of assays known to those skilled in the art can be utilized to detect antibodies which specifically bind to zsig15 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant zsig15 polypeptide.

Antibodies to zsig15 may be used for tagging cells that express zsig15 for isolating zsig15 by affinity purification; for diagnostic assays for determining circulating levels of zsig15 polypeptides; for detecting or quantitating soluble zsig15 as marker of underlying pathology or disease; in analytical methods employing FACS; for screening expression libraries; for generating anti-idiotypic antibodies; and as neutralizing antibodies or as antagonists to block zsig15 activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to zsig15 or fragments thereof may be used in vitro to detect denatured zsig15 or fragments thereof in assays, for example, Western Blots or other assays known in the art.

Antibodies or polypeptides herein can also be directly or indirectly conjugated another moiety, for example, to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, zsig15 polypeptides or anti-zsig15 antibodies, or bioactive fragments or portions thereof, can be coupled to detectable or cytotoxic molecules and delivered to a mammal having cells, tissues or organs that express the anti-complementary molecule.

Suitable detectable moieties may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

In another embodiment, zsig15-cytokine fusion proteins or antibody-cytokine fusion proteins can be used for enhancing in vivo killing of target tissues (for example, blood, colon, breast and bone marrow cancers) if the zsig15 polypeptide or anti-zsig15 antibody targets the hyperproliferative cell (See, generally, Hornick et al., *Blood* 89:4437–47, 1997). They described fusion proteins enable targeting of a cytokine to a desired site of action, thereby providing an elevated local concentration of cytokine. Suitable zsig15 polypeptides or anti-zsig15 antibodies target an undesirable cell or tissue (i.e., a tumor or a leukemia), and the fused cytokine mediated improved target cell lysis by effector cells. Suitable cytokines for this purpose include interleukin 2 and granulocyte-macrophage colony-stimulating factor (GM-CSF), for instance.

The bioactive polypeptide or antibody conjugates described herein can be delivered intravenously, intraarterially or intraductally, or may be introduced locally at the intended site of action.

Molecules of the present invention can be used to identify and isolate receptors involved in cancer metastases. For example, proteins and peptides of the present invention can be immobilized on a column and membrane preparations run over the column (*Immobilized Affinity Ligand Techniques*, Hermanson et al., eds., Academic Press, San Diego, Calif., 1992, pp.195–202). Proteins and peptides can also be radio-labeled (*Methods in Enzymol.*, vol. 182, "Guide to Protein Purification", M. Deutscher, ed., Acad. Press, San Diego, 1990, 721–737) or photoaffinity labeled (Brunner et al., *Ann. Rev. Biochem.* 62:483–514, 1993 and Fedan et al., *Biochem. Pharmacol.* 33:1167–1180, 1984) and specific cell-surface proteins can be identified.

The polypeptides, nucleic acid and/or antibodies of the present invention can be used in treatment of disorders associated with prostate, colon or breast cancer. The molecules of the present invention can be used to modulate or to treat or prevent development of pathological conditions. In particular, certain cancers, inflammatory and hyperplastic diseases may be amenable to such diagnosis, treatment or prevention.

Polynucleotides encoding zsig15 polypeptides are useful within gene therapy applications where it is desired to increase or inhibit zsig15 activity. If a mammal has a mutated or absent zsig15 gene, the zsig15 gene can be introduced into the cells of the mammal. In one embodiment, a gene encoding a zsig15 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a zsig15 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Antisense methodology can be used to inhibit zsig15 gene transcription, such as to inhibit cell proliferation in vivo. Polynucleotides that are complementary to a segment of a zsig15-encoding polynucleotide (e.g., a polynucleotide as set forth in SEQ ID NO:1) are designed to bind to zsig15-encoding mRNA and to inhibit translation of such mRNA. Such antisense polynucleotides are used to inhibit expression of zsig15 polypeptide-encoding genes in cell culture or in a subject.

The present invention also provides reagents which will find use in diagnostic applications. For example, the zsig15 gene, a probe comprising zsig15 DNA or RNA or a subsequence thereof can be used to determine if the zsig15 gene is present on chromosome 19 or if a mutation has occurred. Detectable chromosomal aberrations at the zsig15 gene locus include, but are not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; Marian, *Chest* 108:255–65, 1995).

Transgenic mice, engineered to express the zsig15 gene, and mice that exhibit a complete absence of zsig15 gene function, referred to as "knockout mice" (Snouwaert et al., *Science* 257:1083, 1992), may also be generated (Lowell et al., *Nature* 366:740–42, 1993). These mice may be employed to study the zsig15 gene and the protein encoded thereby in an in vivo system.

Radiation hybrid mapping is a somatic cell genetic technique developed for constructing high-resolution, contiguous maps of mammalian chromosomes (Cox et al., *Science* 250:245–50, 1990). Partial or full knowledge of a gene's sequence allows one to design PCR primers suitable for use with chromosomal radiation hybrid mapping panels. Radiation hybrid mapping panels are commercially available which cover the entire human genome, such as the Stanford G3 RH Panel and the GeneBridge 4 RH Panel (Research Genetics, Inc., Huntsville, Ala.). These panels enable rapid, PCR-based chromosomal localizations and ordering of genes, sequence-tagged sites (STSs), and other nonpolymorphic and polymorphic markers within a region of interest. This includes establishing directly proportional physical distances between newly discovered genes of interest and previously mapped markers. The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

Sequence tagged sites (STSs) can also be used independently for chromosomal localization. An STS is a DNA sequence that is unique in the human genome and can be used as a reference point for a particular chromosome or region of a chromosome. An STS is defined by a pair of oligonucleotide primers that are used in a polymerase chain reaction to specifically detect this site in the presence of all other genomic sequences. Since STSs are based solely on DNA sequence they can be completely described within an electronic database, for example, Database of Sequence Tagged Sites (dbSTS), GenBank, (National Center for Biological Information, National Institutes of Health, Bethesda, Md., and can be searched with a gene sequence of interest for the mapping data contained within these short genomic landmark STS sequences.

For pharmaceutical use, the proteins of the present invention are formulated for parenteral, particularly intravenous or subcutaneous, delivery according to conventional methods. Intravenous administration will be by bolus injection or infusion over a typical period of one to several hours. In general, pharmaceutical formulations will include a zsig15 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 µg/kg of patient weight per day, preferably 0.5–20 µg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years.

The invention is further illustrated by the following non-limiting examples.

EXAMPLES

Example 1

Scanning of a cDNA database for cDNAs containing a secretion sequence revealed an expressed sequence tag (EST) that was novel and did not have homology to any known protein. The cDNA is from a human colon cDNA library.

Confirmation of the EST sequence was made by excising the cDNA from its plasmid using a Sal I (nucleotide 1 of SEQ ID NO: 1) to Not I (nucleotide 1726 of SEQ ID NO: 1) and doing a sequence analyses of the cDNA from which the EST originated. The analyses revealed that the cDNA encompassed the entire coding region of the DNA encoding zsig15.

Example 2

Northerns were performed using Human Multiple Tissue Blots and Human RNA Master dot blots from Clontech (Palo Alto, Calif.). The probe was approximately 30 bp oligonucleotide ZC11366 (SEQ ID NO: 3). The probe was end labeled using T4 Polynucleotide Kinase (Life Technologies, Inc., Gaithersburg, Md.) and T4 Polynucleotide Kinase Forward Buffer (Life Technologies, Inc.). The probe was purified using a NUCTRAP push columns (Stratagene, La Jolla, Calif.). EXPRESSHYB (Clontech) solution was used for prehybridization and as a hybridizing solution for the Northern blots. Hybridization took place at 42° C., and the blots were washed in 2×SSC and 0.1% SDS at RT, followed by a wash in 1×SSC and 0.1% SDS at 50° C. After an overnight exposure a third wash at 65° C. in 1×SSC. 0.1 SDS was done. Two transcripts were observed at 1.7 and 2.5 kb with a strong signal in prostate, with weaker signals seen in bone marrow and pancreas, colon mucosal lining and spinal cord. Dot blots revealed positive signals for prostate and bone marrow.

Tumor blots were probed with the insert from clone described previously. The probe was labeled as described previously and the tumor blots were washed at 2×SSC, 0.1% SDS at RT, followed by a wash at 65° C. in 0.1×SSC, 0.1% SDS. The human colon tumor blot (Invitrogen, Carlsbad, Calif.) contained total RNA isolated from human tumor and normal tissues from four different donors, where the normal/tumor pair was excised from the same operational site. Table 5 summarizes the results.

TABLE 5

| sex | age | tumor description | normal expression level | tumor expression level |
|-----|-----|-------------------|-------------------------|------------------------|
| M | 37 | adeno-carcinoma | ++++ | − |
| M | 59 | adeno-carcinoma | +++ | − |
| M | 33 | differentiated adeno-carcinoma | +++ | ++ |
| M | 56 | poorly-moderately differentiated adenocarcinoma | − | ++++ |

The human breast tumor blot (Invitrogen) contained total RNA isolated from human tumor and normal tissues from four different donors, where the normal/tumor pair was excised from the same operational site. Table 6 summarizes the results.

TABLE 6

| sex | age | tumor description | normal expression level | tumor expression level |
|---|---|---|---|---|
| F | 57 | invasive ducal carcinoma | ++ | − |
| F | 50 | invasive ductal carcinoma | + | − |
| M | 51 | invasive ductal carcinoma | − | +++ |
| M | 48 | invasive ductal carcinoma | ++ | − |

These data suggest that zsig15 mRNA is expressed at levels that vary with the cell's or tumor's differentiated state.

Example 3

Zsig15 was mapped to chromosome 19 using the commercially available "GeneBridge 4 Radiation Hybrid Panel" (Research Genetics, Inc., Huntsville, Ala.). The GeneBridge 4 Radiation Hybrid Panel contains DNAs from each of 93 radiation hybrid clones, plus two control DNAs (the HFL donor and the A23 recipient). A publicly available WWW server allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of Zsig15 with the "GeneBridge 4 RH Panel", 25 μl reactions were set up in a 96-well microtiter plate (Stratagene, La Jolla, Calif.) and used in a "RoboCycler Gradient 96" thermal cycler (Stratagene). Each of the 95 PCR reactions consisted of 2.5 μl "10×KlenTaq reaction buffer" (Clontech Laboratories, Inc., Palo Alto, Calif.), 2 μl dNTPs mix (2.5 mM each, Perkin-Elmer, Foster City, Calif.), 1.25 μl sense primer, ZC 11,369, 5' CGG CAA TGG ACC CCT AAG AA 3', 1.25 μl antisense primer, ZC 12,162, (SEQ ID NO: ) 5' TCC TCC TGG CGG CAC ACG AA 3', 2.5 μl "RediLoad" (Research Genetics, Inc., Huntsville, Ala.), 0.5 μl "50×Advantage KlenTaq Polymerase Mix" (Clontech Laboratories, Inc.), 25 ng of DNA from an individual hybrid clone or control and ddH20 for a total volume of 25 μl. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 70° C. and 1.5 minute extension at 72° C., followed by a final 1 cycle extension of 7 minutes at 72° C. The reactions were separated by electrophoresis on a 3% NuSieve GTG agarose gel (FMC Bioproducts, Rockland, Me.).

The results showed that Zsig15 maps 323.29 cR_3000 from the top of the human chromosome 19 linkage group on the WICGR radiation hybrid map. Proximal and distal framework markers were D19S827 and D19S420, respectively. These markers position Zsig15 in the 19q13.2 region on the integrated LDB chromosome 19 map (The Genetic Location Database, University of Southhampton, WWW server:).

Example 4

Creation of Mammalian Expression Vectors zsig15NF/pZP9, zsig15CF/pZP9, soluble zsig15sNF/pZP9, soluble zsig15sCF/pZP9 and zsig15/pZP9

Five expression vectors were prepared for the zsig15 polypeptide, zsig15CF/pZP9 and zsig15NF/pZP9 were designed to express a full length zsig15 polypeptide with a C- or N-terminal FLAG tag (SEQ ID NO:5), zsig15 sNF/pZP9, zsig15 sCF/pZP9 were designed to express a soluble zsig15 polypeptide having an N- or C-terminal FLAG tag, and zsig15/pZP9, was designed to express an untagged zsig15 polypeptide.

ZSIG15/pZP9

An approximately 1726 bp restriction digest fragment of zsig-15 DNA was derived from the clone described in Example 1 above by restriction digest with enzymes Sal I and Not I. The resultant restriction fragment was visualized by agarose gel electrophoresis. A band of the predicted size was excised and the DNA was purified from the gel with a QIAQUICK® column (Qiagen) according the manufacturer's instructions.

The excised, restriction digested zsig15 DNA fragment was subcloned into plasmid pZP9 which had been cut with Xho I and Not I. Plasmid pZP9 (deposited at the American Type Culture Collection, 12301 Parklawn Drive, Rockville, Md.) is a mammalian expression vector containing an expression cassette having the mouse metallothionein-1 promoter, multiple restriction sites for insertion of coding sequences, a stop codon and a human growth hormone terminator. The plasmid also has an E. coli origin of replication, a mammalian selectable marker expression unit having an SV40 promoter, enhancer and origin of replication, a DHFR gene and the SV40 terminator.

The insert and expression vector were ligated overnight at 16° C., followed by electroporation into DH10B competent cells (GIBCO BRL, Gaithersburg, Md.) according to manufacturer's direction. The cells were plated onto LB plates containing 50 mg/ml ampicillin, and incubated at 37° C. overnight. Colonies were screened by PCR using oligonucleotide primers to the vector, ZC13006 (SEQ ID NO:6) and ZC13007 (SEQ ID NO:7). The insert sequence of positive clones was verified by sequence analysis. A large scale plasmid preparation was done using a QIAGEN® Maxi prep kit (Qiagen) according to manufacturer's instructions.

zSIG25CF/pZP9

A 1.3 kb PCR generated zsig15 DNA fragment was created using two rounds of PCR to remove a Bam HI site (nucleotide 423 of SEQ ID NO:1 changed from C to A). Oligonucleotide primers ZC 13809 (SEQ ID NO:8) and ZC13812 (SEQ ID NO:9) were used to generate a ~392 bp 5' fragment. oligonucleotide primers ZC 13804 (SEQ ID NO:10) and ZC13815 (SEQ ID NO:11) were used to generate a ~925 bp overlapping 3' fragment. Zsig15/pZP9 as described above, was used as a template, with an initial denaturation at 94° C. for 1 minute 30 seconds, 12 cycles of 94° C., 10 seconds, 76° C. 20 seconds, 72° C. for 1 minute 30 seconds, followed by a 10 minute extension at 72° C. The resulting fragments were purified using a S-300 MicroSpin column (Pharmacia LKB Biotechnology Inc., Piscataway, N.J.) according the manufacturer's instructions. A second round of PCR was done to join the 5' and 3' fragments using oligonucleotide primers ZC 13809 (SEQ ID NO:8) and ZC13815 (SEQ ID NO:11). The 5' and 3' first round fragments were used as templates for the second round of PCR, with an initial denaturation at 94° C. for 1 minute 30 seconds, 12 cycles of 94° C., 10 seconds, 76° C. 20 seconds, 72° C. for 1 minute 30 seconds, followed by a 10 minute extension at 72° C. The resulting 1.3 kb second round fragment visualized by agarose gel electrophoresis, excised and gel purified using QIAQUICK® column (Qiagen, Inc., Chatsworth, Calif.) according to manufacturer's instruction.

The purified PCR fragment was digested with the restriction enzymes Bam HI and Eco RI, visualized by agarose gel electrophoresis, excised and gel purified using QIAQUICK® column (Qiagen) as above. The restriction fragment was ligated into a Eco RI-Bam HI restriction digested CF/pZP9 expression vector. The zsig15/CFpZP9 expression vector uses the native zsig15 signal peptide, and the FLAG epitope (SEQ ID NO:5) is attached at the C-terminus as a purification aid. Plasmid CF/pZP9 (deposited at the American Type Culture Collection, 12301 Parklawn Drive, Rockville, Md.) is a mammalian expression vector containing an expression cassette having the mouse metallothionein-1 promoter, multiple restriction sites for insertion of coding sequences, a sequence encoding the FLAG tag (SEQ ID NO:5), a stop codon and a human growth hormone terminator. The plasmid also has an *E. coli* origin of replication, a mammalian selectable marker expression unit having an SV40 promoter, enhancer and origin of replication, a DHFR gene and the SV40 terminator.

zSIG25NF/pZP9

A approximately 1.26 kb fragment of ZSIG-15 DNA was derived by two rounds of PCR as described above, removing a Bam HI site by changing nucleotide 423 of SEQ ID NO:1 from C to A and adding a stop codon at the 3' end. In the first round, oligonucleotides ZC13811 (SEQ ID NO:12) and ZC13812 (SEQ ID NO:9) were used, with zsig15/pZP9 as a template, generating an approximately 345 bp 5' fragment. Oligonucleotide primers ZC13804 (SEQ ID NO:10) and ZC13810 (SEQ ID NO:13) were used to generate an approximately 925 bp overlapping 3' fragment. The 5' and 3' first round fragments were used as templates for the second round PCR with oligonucleotide primers ZC13811 (SEQ ID NO:12) and ZC13810 (SEQ ID NO:13). The resulting 1.26 kb second round fragment was visualized by agarose gel electrophoresis, excised and gel purified using QIAQUICK® column (Qiagen, Inc., Chatsworth, Calif.) according to manufacturer's instruction.

The purified PCR fragment was digested with the restriction enzymes Bam HI and Xba I and ligated into a Bam HI/Xba I restriction digested NFpZP9 expression vector as described above. The zsig15 NF/pZP9 vector incorporates the TPA leader and attaches the FLAG tag (SEQ ID NO:5) to the N-terminal of the zsig15 polypeptide-encoding polynucleotide sequence. Plasmid NF/pZP9 (deposited at the American Type Culture Collection, 12301 Parklawn Drive, Rockville, Md.) is a mammalian expression vector containing an expression cassette having the mouse metallothionein-1 promoter, a TPA leader peptide followed by the sequence encoding the FLAG tag (SEQ ID NO:5), multiple restriction sites for insertion of coding sequences, and a human growth hormone terminator. The plasmid also contains an *E. coli* origin of replication, a mammalian selectable marker expression unit having an SV40 promoter, enhancer and origin of replication, a DHFR gene and the SV40 terminator.

zsig15sCF/pZP9

A approximately 1.18 kb soluble ZSIG-15 DNA fragment was derived by two rounds of PCR as described above, removing a Bam HI site by changing nucleotide 423 of SEQ ID NO:1 from C to A and truncating the sequence at amino acid residue 394 (Glu) of SEQ ID NO:2 just prior to the hydrophobic region. In the first round, oligonucleotides ZC13809 (SEQ ID NO:8) and ZC13812 (SEQ ID NO:9) were used, with zsig15/pZP9 as a template, generating an approximately 392 bp 5' fragment. Oligonucleotide primers ZC13804 (SEQ ID NO:10) and ZC13814 (SEQ ID NO:14) were used to generate an approximately 780 bp overlapping 3' fragment. The 5' and 3' first round fragments were used as templates for the second round PCR with oligonucleotide primers ZC13809 (SEQ ID NO:8) and ZC13814 (SEQ ID NO:14). The resulting 1.18 kb second round fragment was visualized by agarose gel electrophoresis, excised and gel purified using QIAQUICK® column (Qiagen, Inc., Chatsworth, Calif.) according to manufacturer's instruction.

zsig15sNF/pZP9

A approximately 1.14 kb soluble ZSIG-15 DNA fragment was derived by two rounds of PCR as described above, removing a Bam HI site by changing nucleotide 423 of SEQ ID NO:1 from C to A and truncating the sequence at amino acid residue 394 (Glu) of SEQ ID NO:2 just prior to the hydrophobic region and adding a stop codon at the 3' end. In the first round, oligonucleotides ZC13811 (SEQ ID NO:12) and ZC13812 (SEQ ID NO:9) were used, with zsig15/pZP9 as a template, to generate an approximately 345 bp 5' fragment. Oligonucleotide primers ZC13804 (SEQ ID NO:10) and ZC13813 (SEQ ID NO:15) were used to generate an approximately 780 bp overlapping 3' fragment. The 5' and 3' first round fragments were used as templates for the second round PCR with oligonucleotide primers ZC13813 (SEQ ID NO:15) and ZC13811 (SEQ ID NO:12). The resulting approximately 1.14 kb second round fragment was visualized by agarose gel electrophoresis, excised and gel purified using QIAQUICK® column (Qiagen, Inc.) according to manufacturer's instruction.

Approximately 20–30 ng of each of the restriction digested inserts and 0.05–0.06 pm of the corresponding vectors were independently ligated overnight at 16° C. 1.2 μl of each ligation reaction was independently electroporated into 38 μl of DH10B competent cells (GIBCO BRL, Gaithersburg, Md.) according to manufacturer's direction and plated onto LB plates containing 50 mg/ml ampicillin, and incubated overnight. Colonies were screened by PCR using oligonucleotide primers to the expression vectors, ZC13006 (SEQ ID NO:6) and ZC13007 (SEQ ID NO:7). The insert sequence of positive clones were verified by sequence analysis. A large scale plasmid preparation was done using a QIAGEN® Maxi prep kit (Qiagen) according to manufacturer's instructions.

Example 5
Mammalian Expression of zsig15

BHK 570 cells (ATCC NO: CRL-10314) were plated in 10 cm tissue culture dishes and allowed to grow to approximately 50 to 70% confluency overnight at 37° C., 5% $CO_2$, in DMEM/FBS media (DMEM, Gibco/BRL High Glucose, (Gibco BRL, Gaithersburg, Md.), 5% fetal bovine serum (Hyclone, Logan, Utah), 1 μM L-glutamine (JRH Biosciences, Lenexa, Kans.), 1 μM sodium pyruvate (Gibco BRL)). The cells were then transfected with the plasmid zsig15NF/pZP9 (full length N-terminal FLAG tag), zsig15CF/pZP9 (full length C-terminal FLAG tag), zsig15sNF/pZP9 (soluble N-terminal FLAG tag) and zsig15sCF/pZP9 (soluble C-terminal FLAG tag), using Lipofectamine™ (Gibco BRL), in serum free (SF) media formulation (DMEM, 10 mg/ml transferrin, 5 mg/ml insulin, 2 mg/ml fetuin, 1% L-glutamine and 1% sodium pyruvate). Sixteen micrograms of each expression construct were separately diluted into 15 ml tubes to a total final volume of 640 μl with SF media. In separate tubes, 35 μl of Lipofectamine™ (Gibco BRL) was mixed with 605 μl of SF medium. The Lipofectamine™ mix was added to the expression construct mix and allowed to incubate approximately 30 minutes at room temperature. Five milliliters of SF media was added to the DNA:Lipofectamine™ mixture. Three plates of cells were rinsed once with 5 ml of SF media, aspirated, and the DNA:Lipofectamine™ mixture was added. The cells were incubated at 37° C. for five hours, then 6.4 ml of DMEM/10% FBS, 1% PSN media was added to each plate. The plates were incubated at 37° C. overnight and the DNA:Lipofectamine™ mixture was replaced with fresh FBS/DMEM media the next day. On day 2 post-transfection, the cells were split into the selection media (DMEM/FBS media from above with the addition of 1 μM methotrexate (Sigma Chemical Co., St. Louis, Mo.)) in 150 mm plates at 1:10, 1:20 and 1:50. The cells were refed at day 5 post-transfection with fresh selection media.

Approximately 10–12 days post-transfection, two 150 mm culture dishes of methotrexate resistant colonies were chosen, the media aspirated, the plates washed with 10 ml serum-free ESTEP 2 media (668.7 g/50 L DMEM (Gibco), 5.5 g/50 L pyruvic acid, sodium salt 96% (Mallinckrodt), 185.0 g/50 L NaHCO$_3$ (Mallinkrodt), 5.0 mg/ml, 25 ml/50 L insulin, 10.0 mg/ml and 25 ml/50 L transferrin). The wash media was aspirated and replaced with 5 ml serum-free ESTEP 2. Sterile Teflon mesh (Spectrum Medical Industries, Los Angeles, Calif.) pre-soaked in serum-free ESTEP 2 was then placed over the cells. A sterile nitrocellulose filter pre-soaked in serum-free ESTEP 2 was then placed over the mesh. Orientation marks on the nitrocellulose were transferred to the culture dish. The plates were then incubated for 5–6 hours in a 37° C., 5% CO$_2$ incubator. Following incubation, the filter was removed, and the media aspirated and replaced with DMEM/5% FBS, 1×PSN (Gibco BRL) media. The filters were blocked in 2.5% nonfat dry milk/Western A buffer (Western A: 50 mM Tris pH 7.4, 5 mM EDTA, 0.05% NP-40, 150 mM NaCl and 0.25% gelatin) overnight at 4° C. on a rotating shaker. The filter was then incubated with a goat anti-human FLAG-HRP conjugate at a 1:4000 dilution (5 μl antibody in 20 ml buffer) in 2.5% nonfat dry milk/Western A buffer (Western A: 50 mM Tris pH 7.4, 5 mM EDTA, 0.05% NP-40, 150 mM NaCl and 0.25% gelatin) at room temperature for 1 hour on a rotating shaker. The filter was then washed three times at room temperature in PBS plus 0.1% Tween 20, 15 minutes per wash. The filter was developed with ECL reagent (Amersham Corp., Arlington Heights, Ill.) according the manufacturer's directions and exposed to film (Hyperfilm ECL, Amersham) for approximately 5 minutes.

The film was aligned with the plate containing the colonies. Using the film as a guide, suitable colonies were selected. Sterile, 3 mm coloning discs (PGC Scientific Corp., Frederick, Md.) were soaked in trypsin, and placed on the colonies. The colonies were transferred into 200 μl of selection medium in a 96 well plate. A series of seven, two-fold dilutions were carried out for each colony. The 150 mm culture dish was then trypsinized and the remainder of the cells were pooled and split into two T162 flasks containing DMEM/5% FBS and 1 μM MTX media. The cells were grown for one week at 37° C. at which time the wells which received the lowest dilution of cells which are now at the optimum density were selected, trypsinized and transferred to a 12 well plate containing selection media.

The clones were expanded directly from the 12 well plate to 2 T-75 flasks. One flask from each clone is grown in serum-free ESTEP 2 and the media harvested for Western Blot analysis. Clones of each of the expression constructs, based on Western blot analysis were selected, pooled together and transferred to large scale culture.

Example 6
Large Scale Mammalian Expression of zsig15

One T-162 flask, containing confluent cells expressing zsig15s/NF and one flask containing zsig15s/CF expressing cells, obtained from the expression procedure described above, were expanded into five T-162 flasks. One of the five resulting flasks was used to freeze down four cryovials, and the other four flasks were used to generate a Nunc cell factory.

The cells from the four T-162 flasks of zsig15s/NF and zsig15s/CF were combined and used to seed two Nunc cell factories (10 layers, commercially available from VWR). Briefly, the cells from the T-162 flasks described above were detached using trypsin, pooled, and added to 1.5 liters ESTEP1 media (668.7g/50 L DMEM (Gibco), 5.5 g/50 L pyruvic acid, sodium salt 96% (Mallinckrodt), 185.0 g/50 L NaHCO$_3$ (Mallinkrodt), 5.0 mg/ml and 25 ml/50 L insulin (JRH Biosciences), 10.0 mg/ml and 25 ml/50 L transferrin (JRH Biosciences), 2.5 L/50 L fetal bovine serum (characterized) (Hyclone), 1 μM MTX, with pH adjusted to 7.05+/−0.05) prewarmed to 37° C. The media containing the cells was then poured into the Nunc cell factories via a funnel. The cell factories were placed in a 37° C./5.0% CO$_2$ incubator.

At 80–100% confluence, a visual contamination test (phenol red color change) was performed on the Nunc cell factories. Since no contamination was observed, supernatant from the confluent factories was poured into a small harvest container, sampled and discarded. The adherent cells were then washed once with 400 ml PBS. To detach the cells from the factories, 100 mls of trypsin was added to each and removed and the cells were then incubated for 5 to 10 minutes in the residual trypsin. The cells were collected following two, 200 ml washes of ESTEP1 media. To each of ten ESTEP1 media-containing bottles (1.5 liters each, at 37° C.) was added 40 mls of collected cells. One 1.5 liter bottle was then used to fill one Nunc factory. Each cell factory was placed in a 37° C./5.0% CO$_2$ incubator.

At 80–90% confluence, a visual contamination test (phenol red color change) was performed on the Nunc cell factories. Since no contamination was observed, supernatant from the confluent factories was poured into a small harvest container, sampled and discarded. Cells were then washed once with 400 ml PBS. 1.5 liters of ESTEP2 media (668.7 g/50 L DMEM (Gibco), 5.5 g/50 L pyruvic acid, sodium salt 96% (Mallinckrodt), 185.0 g/50 L NaHCO$_3$ (Mallinkrodt), 5.0 mg/ml, 25 ml/50 L insulin, 10.0 mg/ml and 25 ml/50 L transferrin) was added to each Nunc cell factory. The cell factories were incubated at 37° C./5.0% CO$_2$.

At approximately 40 hours a visual contamination test (phenol red color change) was performed on the Nunc cell factories. Supernatant from each factory was poured into small harvest containers. A total of 15 liters was collected from all 10 factories. Fresh serum-free media (1.5 liters) was poured into each Nunc cell factory, and the factories were incubated at 37° C./5.0% CO$_2$. One ml of supernatant harvest was transferred to a microscope slide, and subjected to microscopic analysis for contamination. The contents of the small harvest containers for each factory were pooled and immediately filtered. A second harvest was then performed, substantially as described above at 50 hours (15 L were obtained) and the cell factories were discarded thereafter. An aseptically assembled filter train apparatus was used for aseptic filtration of the harvest supernatant (conditioned media). Assembly was a follows: tubing was wire-tied to an Opti-Cap filter (Millipore Corp., Bedford, Mass.) and a Gelman Supercap 50 filter (Gelman Sciences, Ann Arbor, Mich.). The Supercap 50 filter was also attached to a sterile capped container located in a hood; tubing located upstream of the Millipore Opti-cap filter was inserted into a peristaltic pump; and the free end of the tubing was placed in the large harvest container. The peristaltic pump was run between 200 and 300 rpm, until all of the conditioned media passed through the 0.22 μm final filter into a sterile collection container. The filtrate was placed in a 4° C. cold room pending purification. The media was concentrated 10× with a Millipore 5 kDA cut off concentrator (Millipore Corp., Bedford, Mass.) according to manufacturer's direction and subjected to Western Blot analysis using an anti-FLAG tag antibody (Kodak).

Example 7

Unless otherwise noted, all operations are carried out at 4° C. The following procedure is used to purify zsig15 containing N-terminal or C-terminal flag tags. A total of 25 liters of conditioned media from baby hamster kidney (BHK) cells is sequentially sterile filtered through a 4 inch, 0.2 mM Millipore (Bedford, Mass.) OptiCap capsule filter and a 0.2 mM Gelman (Ann Arbor, Mich.) Supercap 50. The material is concentrated to about 1.3 liters using an Amicon (Beverly, Mass.) DC 10 L concentrator fitted with a 3000 kDa cutoff membrane. The concentrated material is sterile-filtered again with is be added to the concentrated conditioned media to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), 0.001 mM pepstatin (Boehringer-Mannheim) and 0.4 mM Pefabloc (Boehringer-Mannheim). A 25.0 ml sample of anti-Flag Sepharose (Eastman Kodak, Rochester, N.Y.) is added to the sample for batch adsorption and the mixture is gently agitated on a Wheaton (Millville, N.J.) roller culture apparatus for 18.0 h at 4° C.

The mixture is then poured into a 5.0×20.0 cm Econo-Column (Bio-Rad, Laboratories, Hercules, Calif.) and the gel is washed with 30 column volumes of phosphate buffered saline (PBS). The unretained flow-through fraction is discarded. Once the absorbance of the effluent at 280 nM is less than 0.05, flow-through the column is reduced to zero and the anti-Flag Sepharose gel is washed batchwise with 2.0 column volumes of PBS containing 0.2 mg/ml of Flag peptide, N-AspTyrLysAspAspAspAspLys-C (Seq. ID. No. 5; Eastman Kodak). After 1.0 h at 4° C., flow is resumed and the eluted protein is collected. This fraction is referred to as the peptide elution. The anti-Flag Sepharose gel is washed with 2.0 column volumes of 0.1M glycine, pH 2.5, and the glycine wash is collected separately. The pH of the glycine-eluted fraction is adjusted to 7.0 by the addition of a small volume of 10×PBS and is stored at 4° C. for future analysis if needed.

The peptide elution is concentrated to 5.0 ml using a 5,000 molecular weight cutoff membrane concentrator (Millipore, Bedford, Mass.), according to the manufacturer's instructions. The concentrated peptide elution is separated from free peptide by chromatography on a 1.5×50 cm Sephadex G-50 (Pharmacia, Piscataway, N.J.) column equilibrated in PBS at a flow rate of 1.0 ml/min using a BioCad Sprint HPLC system (PerSeptive BioSystems, Framingham, Mass.). Two-ml fractions are collected and the absorbance at 280 nM is monitored. The first peak of material absorbing at 280 nM and eluting near the void volume of the column is collected. The purity of the zsig15 NF and zsig15 CF is monitored by SDS-PAGE and Western analysis with anti-Flag M2 antibodies (Kodak).

The protein concentration of the purified proteins is performed by BCA analysis (Pierce, Rockford, Ill.) and the material is aliquoted, and stored at −80° C.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polynucleotide molecule selected from the group consisting of:
    (a) a polynucleotide molecule comprising a nucleotide sequence as shown in SEQ ID NO: 1 from nucleotide 97 to nucleotide 1215;
    (b) a polynucleotide molecule that encodes a polypeptide that is the amino acid sequence of SEQ ID NO: 2 from amino acid residue 22 (Leu) to amino acid residue 394 (Glu); and
    (c) a polynucleotide molecule comprising a degenerate nucleotide sequence of (a) or (b).

2. The isolated polynucleotide molecule of claim 1, wherein the polynucleotide molecule comprises a nucleotide sequence as shown in SEQ ID NO: 1 from nucleotide 97 to nucleotide 1344, or a polynucleotide molecule that encodes a polypeptide that is the amino acid sequence of SEQ ID NO: 2 from residues 22 to 437.

3. The isolated polynucleotide molecule of claim 1, wherein the polynucleotide molecule comprises a nucleotide sequence as shown in SEQ ID NO: 1 from nucleotide 79 to nucleotide 1344, or a polynucleotide molecule that encodes a polypeptide that is the amino acid sequence of SEQ ID NO: 2 from residues 16–437.

4. The isolated polynucleotide molecule of claim 1, wherein the polynucleotide molecule comprises a nucleotide sequence as shown in SEQ ID NO: 1 from nucleotide 34 to nucleotide 1344, or polynucleotide molecule that encodes a polypeptide that is the amino acid sequence of SEQ ID NO: 2 from residues 1 to 347.

5. An isolated polynucleotide molecule comprising a sequence of nucleotides from nucleotide 97 to nucleotide 582 as shown in SEQ ID NO: 1.

6. An isolated polynucleotide molecule comprising a sequence of nucleotides from nucleotide 655 to nucleotide 1215 of SEQ ID NO: 1.

7. The isolated polynucleotide molecule of claim 6, wherein the polynucleotide molecules comprise a sequence of nucleotides from nucleotide 655 to nucleotide 1344 of SEQ ID NO: 1.

8. An isolated polynucleotide molecule encoding a fusion protein comprising a first polypeptide and a second polypeptide, said first polypeptide encoded by a sequence of nucleotides as shown in SEQ ID NO: 1 from nucleotide 97 to nucleotide 582, and said second polypeptide encoded by a sequence of nucleotides as shown in SEQ ID NO: 1 from nucleotide 655 to nucleotide 1215.

9. The isolated polynucleotide molecule of claim 1, wherein the polynucleotide is DNA.

10. An expression vector comprising the following operably linked elements:

a transcription promoter;

a polynucleotide molecule according to claim 1 and a transcription terminator.

11. An expression vector comprising the following operably linked elements:

a transcription promoter;

a polynucleotide molecule according to claim 5; and a transcription terminator.

12. An expression vector comprising the following operably linked elements:

a transcription promoter;

a polynucleotide molecule according to claim 6; and a transcription terminator.

13. An expression vector comprising the following operably linked elements:

a transcription promoter;

a polynucleotide molecule according to claim 7; and a transcription terminator.

14. A cultured cell into which has been introduced an expression vector according to claim 10, 11, 12 or 13, wherein said cell expresses the polypeptide encoded by the polynucleotide molecule.

15. A method of producing a polypeptide comprising:

culturing a cell into which has been introduced an expression vector according to claim 10, 11, 12 or 13, whereby said cell expresses a polypeptide encoded by the polynucleotide molecule; and recovering the polypeptide.

* * * * *

UNITED STATES PATENT AND TRADEMARK OFFICE
CERTIFICATE OF CORRECTION

PATENT NO. : 6,084,088
DATED : July 4, 2000
INVENTOR(S) : Paul O. Sheppard, et. al.

It is certified that error appears in the above-indentified patent and that said Letters Patent is hereby corrected as shown below:

On the cover page at Related U.S. Application Data, please delete "May 6, 1999" and insert therefor --May 6, 1997--.

Signed and Sealed this

Tenth Day of April, 2001

Attest:

NICHOLAS P. GODICI

*Attesting Officer*     *Acting Director of the United States Patent and Trademark Office*

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 1733 base pairs
      (B) TYPE: nucleic acid
      (C) STRANDEDNESS: single
      (D) TOPOLOGY: linear (ix) FEATURE:
      (A) NAME/KEY: Coding Sequence
      (B) LOCATION: 34...1344
      (D) OTHER INFORMATION:

(xi) SEQUENCE DESCRIPTION: SEQ ID NO:1:

```
GTCGACCCAC GCGTCCGCAG CCACAGACGG GTC ATG AGC GCG GTA TTA CTG CTG        54
                                    Met Ser Ala Val Leu Leu Leu
                                     1               5

GCC CTC CTG GGG TTC ATC CTC CCA CTG CCA GGA GTG CAG GCG CTG CTC        102
Ala Leu Leu Gly Phe Ile Leu Pro Leu Pro Gly Val Gln Ala Leu Leu
        10                  15                  20

TGC CAG TTT GGG ACA GTT CAG CTT GTG TGG AAG GTG TCC GAC CTA CCC        150
Cys Gln Phe Gly Thr Val Gln Leu Val Trp Lys Val Ser Asp Leu Pro
```

-continued

```
             25                  30                  35
CGG CAA TGG ACC CCT AAG AAC ACC AGC TGC GAC AGC GGC TTG GGG TGC    198
Arg Gln Trp Thr Pro Lys Asn Thr Ser Cys Asp Ser Gly Leu Gly Cys
 40              45                  50                  55

CAG GAC ACG TTG ATG CTC ATT GAG AGC GGA CCC CAA GTG AGC CTG GTG    246
Gln Asp Thr Leu Met Leu Ile Glu Ser Gly Pro Gln Val Ser Leu Val
                 60                  65                  70

CTC TCC AAG GGC TGC ACG GAG GCC AAG GAC CAG GAG CCC CGC GTC ACT    294
Leu Ser Lys Gly Cys Thr Glu Ala Lys Asp Gln Glu Pro Arg Val Thr
             75                  80                  85

GAG CAC CGG ATG GGC CCC GGC CTC TCC CTG ATC TCC TAC ACC TTC GTG    342
Glu His Arg Met Gly Pro Gly Leu Ser Leu Ile Ser Tyr Thr Phe Val
                 90                  95                 100

TGC CGC CAG GAG GAC TTC TGC AAC AAC CTC GTT AAC TCC CTC CCG CTT    390
Cys Arg Gln Glu Asp Phe Cys Asn Asn Leu Val Asn Ser Leu Pro Leu
            105                 110                 115

TGG GCC CCA CAG CCC CCA GCA GAC CCA GGA TCC TTG AGG TGC CCA GTC    438
Trp Ala Pro Gln Pro Pro Ala Asp Pro Gly Ser Leu Arg Cys Pro Val
120                 125                 130                 135

TGC TTG TCT ATG GAA GGC TGT CTG GAG GGG ACA ACA GAA GAG ATC TGC    486
Cys Leu Ser Met Glu Gly Cys Leu Glu Gly Thr Thr Glu Glu Ile Cys
                140                 145                 150

CCC AAG GGG ACC ACA CAC TGT TAT GAT GGC CTC CTC AGG CTC AGG GGA    534
Pro Lys Gly Thr Thr His Cys Tyr Asp Gly Leu Leu Arg Leu Arg Gly
            155                 160                 165

GGA GGC ATC TTC TCC AAT CTG AGA GTC CAG GGA TGC ATG CCC CAG CCA    582
Gly Gly Ile Phe Ser Asn Leu Arg Val Gln Gly Cys Met Pro Gln Pro
                170                 175                 180

GGT TGC AAC CTG CTC AAT GGG ACA CAG GAA ATT GGG CCC GTG GGT ATG    630
Gly Cys Asn Leu Leu Asn Gly Thr Gln Glu Ile Gly Pro Val Gly Met
185                 190                 195

ACT GAG AAC TGC AAT AGG AAA GAT TTT CTG ACC TGT CAT CGG GGG ACC    678
Thr Glu Asn Cys Asn Arg Lys Asp Phe Leu Thr Cys His Arg Gly Thr
200                 205                 210                 215

ACC ATT ATG ACA CAC GGA AAC TTG GCT CAA GAA CCC ACT GAT TGG ACC    726
Thr Ile Met Thr His Gly Asn Leu Ala Gln Glu Pro Thr Asp Trp Thr
                220                 225                 230

ACA TCG AAT ACC GAG ATG TGC GAG GTG GGG CAG GTG TGT CAG GAG ACG    774
Thr Ser Asn Thr Glu Met Cys Glu Val Gly Gln Val Cys Gln Glu Thr
            235                 240                 245

CTG CTG CTC ATA GAT GTA GGA CTC ACA TCA ACC CTG GTG GGG ACA AAA    822
Leu Leu Leu Ile Asp Val Gly Leu Thr Ser Thr Leu Val Gly Thr Lys
                250                 255                 260

GGC TGC AGC ACT GTT GGG GCT CAA AAT TCC CAG AAG ACC ACC ATC CAC    870
Gly Cys Ser Thr Val Gly Ala Gln Asn Ser Gln Lys Thr Thr Ile His
265                 270                 275

TCA GCC CCT CCT GGG GTG CTT GTG GCC TCC TAT ACC CAC TTC TGC TCC    918
Ser Ala Pro Pro Gly Val Leu Val Ala Ser Tyr Thr His Phe Cys Ser
280                 285                 290                 295

TCG GAC CTG TGC AAT AGT GCC AGC AGC AGC GTT CTG CTG AAC TCC        966
Ser Asp Leu Cys Asn Ser Ala Ser Ser Ser Val Leu Leu Asn Ser
                300                 305                 310

CTC CCT CCT CAA GCT GCC CCT GTC CCA GGA GAC CGG CAG TGT CCT ACC    1014
Leu Pro Pro Gln Ala Ala Pro Val Pro Gly Asp Arg Gln Cys Pro Thr
            315                 320                 325

TGT GTG CAG CCC CTT GGA ACC TGT TCA AGT GGC TCC CCC CGA ATG ACC    1062
Cys Val Gln Pro Leu Gly Thr Cys Ser Ser Gly Ser Pro Arg Met Thr
                330                 335                 340

TGC CCC AGG GGC GCC ACT CAT TGT TAT GAT GGG TAC ATT CAT CTC TCA    1110
```

```
        Cys Pro Arg Gly Ala Thr His Cys Tyr Asp Gly Tyr Ile His Leu Ser
            345                 350                 355

GGA GGT GGG CTG TCC ACC AAA ATG AGC ATT CAG GGC TGC GTG GCC CAA          1158
Gly Gly Gly Leu Ser Thr Lys Met Ser Ile Gln Gly Cys Val Ala Gln
360                 365                 370                 375

CCT TCC AGC TTC TTG TTG AAC CAC ACC AGA CAA ATC GGG ATC TTC TCT          1206
Pro Ser Ser Phe Leu Leu Asn His Thr Arg Gln Ile Gly Ile Phe Ser
                380                 385                 390

GCG CGT GAG AAG CGT GAT GTG CAG CCT CCT GCC TCT CAG CAT GAG GGA          1254
Ala Arg Glu Lys Arg Asp Val Gln Pro Pro Ala Ser Gln His Glu Gly
            395                 400                 405

GGT GGG GCT GAG GGC CTG GAG TCT CTC ACT TGG GGG GTG GGG CTG GCA          1302
Gly Gly Ala Glu Gly Leu Glu Ser Leu Thr Trp Gly Val Gly Leu Ala
        410                 415                 420

CTG GCC CCA GCG CTG TGG TGG AGA GTG GTT TGC CCT TCC TGC TAACTCTAT        1353
Leu Ala Pro Ala Leu Trp Trp Arg Val Val Cys Pro Ser Cys
    425                 430                 435

TACCCCCACG ATTCTTCACC GCTGCTGACC ACCCACACTC AACCTCCCTC TGACCTCATA        1413

ACCTAATGGC CTTGGACACC AGATTCTTTC CCATTCTGTC CATGAATCAT CTTCCCCACA        1473

CACAATCATT CATATCTATT CACCTAACAG CAACACTGGG GAGAGCCTGG AGCATCCGGA        1533

CTTGCCCTAT GGGAGAGGGG ACGCTGGAGG AGTGGCTGCA TGTATCTGAT AATACAGACC        1593

CTGTCCTTTC TCCCAAAAAA AAAAAAAAAA AAAAAAAAAA AAAAAAAAAA AAAAAAAAAA        1653

AAAAAAAAAA AAAAAAAAAA AAAAAAAAAA AAAAAAAAAA AAAAAAAAAA AAAAAAAAAA        1713

AAAAAAAAAA GGGCGGCCGC                                                     1733

(2) INFORMATION FOR SEQ ID NO:2:

(i) SEQUENCE CHARACTERISTICS:
        (A) LENGTH: 437 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

Met Ser Ala Val Leu Leu Ala Leu Leu Gly Phe Ile Leu Pro Leu
1               5                   10                  15

Pro Gly Val Gln Ala Leu Leu Cys Gln Phe Gly Thr Val Gln Leu Val
                20                  25                  30

Trp Lys Val Ser Asp Leu Pro Arg Gln Trp Thr Pro Lys Asn Thr Ser
            35                  40                  45

Cys Asp Ser Gly Leu Gly Cys Gln Asp Thr Leu Met Leu Ile Glu Ser
    50                  55                  60

Gly Pro Gln Val Ser Leu Val Leu Ser Lys Gly Cys Thr Glu Ala Lys
65                  70                  75                  80

Asp Gln Glu Pro Arg Val Thr Glu His Arg Met Gly Pro Gly Leu Ser
                85                  90                  95

Leu Ile Ser Tyr Thr Phe Val Cys Arg Gln Glu Asp Phe Cys Asn Asn
            100                 105                 110

Leu Val Asn Ser Leu Pro Leu Trp Ala Pro Gln Pro Pro Ala Asp Pro
        115                 120                 125

Gly Ser Leu Arg Cys Pro Val Cys Leu Ser Met Glu Gly Cys Leu Glu
    130                 135                 140
```

-continued

```
Gly Thr Thr Glu Glu Ile Cys Pro Lys Gly Thr Thr His Cys Tyr Asp
145                 150                 155                 160

Gly Leu Leu Arg Leu Arg Gly Gly Ile Phe Ser Asn Leu Arg Val
                165                 170                 175

Gln Gly Cys Met Pro Gln Pro Gly Cys Asn Leu Leu Asn Gly Thr Gln
                180                 185                 190

Glu Ile Gly Pro Val Gly Met Thr Glu Asn Cys Asn Arg Lys Asp Phe
                195                 200                 205

Leu Thr Cys His Arg Gly Thr Thr Ile Met Thr His Gly Asn Leu Ala
                210                 215                 220

Gln Glu Pro Thr Asp Trp Thr Thr Ser Asn Thr Glu Met Cys Glu Val
225                 230                 235                 240

Gly Gln Val Cys Gln Glu Thr Leu Leu Leu Ile Asp Val Gly Leu Thr
                245                 250                 255

Ser Thr Leu Val Gly Thr Lys Gly Cys Ser Thr Val Gly Ala Gln Asn
                260                 265                 270

Ser Gln Lys Thr Thr Ile His Ser Ala Pro Pro Gly Val Leu Val Ala
                275                 280                 285

Ser Tyr Thr His Phe Cys Ser Ser Asp Leu Cys Asn Ser Ala Ser Ser
290                 295                 300

Ser Ser Val Leu Leu Asn Ser Leu Pro Pro Gln Ala Ala Pro Val Pro
305                 310                 315                 320

Gly Asp Arg Gln Cys Pro Thr Cys Val Gln Pro Leu Gly Thr Cys Ser
                325                 330                 335

Ser Gly Ser Pro Arg Met Thr Cys Pro Arg Gly Ala Thr His Cys Tyr
                340                 345                 350

Asp Gly Tyr Ile His Leu Ser Gly Gly Leu Ser Thr Lys Met Ser
                355                 360                 365

Ile Gln Gly Cys Val Ala Gln Pro Ser Ser Phe Leu Leu Asn His Thr
                370                 375                 380

Arg Gln Ile Gly Ile Phe Ser Ala Arg Glu Lys Arg Asp Val Gln Pro
385                 390                 395                 400

Pro Ala Ser Gln His Glu Gly Gly Ala Glu Gly Leu Glu Ser Leu
                405                 410                 415

Thr Trp Gly Val Gly Leu Ala Leu Ala Pro Ala Leu Trp Trp Arg Val
                420                 425                 430

Val Cys Pro Ser Cys
            435
```

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:3:

GCTGGTGTTC TTAGGGGTCC ATTGCCGGGG                                            30

(2) INFORMATION FOR SEQ ID NO:4:

(i) SEQUENCE CHARACTERISTICS:
        (A) LENGTH: 1311 base pairs
        (B) TYPE: nucleic acid
        (C) STRANDEDNESS: double
        (D) TOPOLOGY: linear -continued (xi) SEQUENCE DESCRIPTION: SEQ ID NO:4:

```
ATGWSNGCNG TNYTNYTNYT NGCNYTNYTN GGNTTYATHY TNCCNYTNCC NGGNGTNCAR     60
GCNYTNYTNT GYCARTTYGG NACNGTNCAR YTNGTNTGGA ARGTNWSNGA YYTNCCNMGN    120
CARTGGACNC CNAARAAYAC NWSNTGYGAY WSNGGNYTNG GNTGYCARGA YACNYTNATG    180
YTNATHGARW SNGGNCCNCA RGTNWSNYTN GTNYTNWSNA ARGGNTGYAC NGARGCNAAR    240
GAYCARGARC CNMGNGTNAC NGARCAYMGN ATGGGNCCNG GNYTNWSNYT NATHWSNTAY    300
ACNTTYGTNT GYMGNCARGA RGAYTTYTGY AAYAAYYTNG TNAAYWSNYT NCCNYTNTGG    360
GCNCCNCARC CNCCNGCNGA YCCNGGNWSN YTNMGNTGYC CNGTNTGYYT NWSNATGGAR    420
GGNTGYYTNG ARGGNACNAC NGARGARATH TGYCCNAARG GNACNACNCA YTGYTAYGAY    480
GGNYTNYTNM GNYTNMGNGG NGGNGGNATH TTYWSNAAYY TNMGNGTNCA RGGNTGYATG    540
CCNCARCCNG GNTGYAAYYT NYTNAAYGGN ACNCARGARA THGGNCCNGT NGGNATGACN    600
GARAAYTGYA AYMGNAARGA YTTYYTNACN TGYCAYMGNG GNACNACNAT HATGACNCAY    660
GGNAAYYTNG CNCARGARCC NACNGAYTGG ACNACNWSNA AYACNGARAT GTGYGARGTN    720
GGNCARGTNT GYCARGARAC NYTNYTNYTN ATHGAYGTNG GNYTNACNWS NACNYTNGTN    780
GGNACNAARG GNTGYWSNAC NGTNGGNGCN CARAAYWSNC ARAARACNAC NATHCAYWSN    840
GCNCCNCCNG GNGTNYTNGT NGCNWSNTAY ACNCAYTTYT GYWSNWSNGA YYTNTGYAAY    900
WSNGCNWSNW SNWSNWSNGT NYTNYTNAAY WSNYTNCCNC CNCARGCNGC NCCNGTNCCN    960
GGNGAYMGNC ARTGYCCNAC NTGYGTNCAR CCNYTNGGNA CNTGYWSNWS NGGNWSNCCN   1020
MGNATGACNT GYCCNMGNGG NGCNACNCAY TGYTAYGAYG GNTAYATHCA YYTNWSNGGN   1080
GGNGGNYTNW SNACNAARAT GWSNATHCAR GGNTGYGTNG CNCARCCNWS NWSNTTYYTN   1140
YTNAAYCAYA CNMGNCARAT HGGNATHTTY WSNGCNMGNG ARAARMGNGA YGTNCARCCN   1200
CCNGCNWSNC ARCAYGARGG NGGNGGNGCN GARGGNYTNG ARWSNYTNAC NTGGGGNGTN   1260
GGNYTNGCNY TNGCNCCNGC NYTNTGGTGG MGNGTNGTNT GYCCNWSNTG Y            1311
```

(2) INFORMATION FOR SEQ ID NO:5:

(i) SEQUENCE CHARACTERISTICS:
(A) LENGTH: 8 amino acids
(B) TYPE: amino acid
(C) STRANDEDNESS: single
(D) TOPOLOGY: linear (xi) SEQUENCE DESCRIPTION: SEQ ID NO:5:

```
Asp Tyr Lys Asp Asp Asp Asp Lys
 1               5
```

(2) INFORMATION FOR SEQ ID NO:6:

(i) SEQUENCE CHARACTERISTICS:
(A) LENGTH: 20 base pairs
(B) TYPE: nucleic acid
(C) STRANDEDNESS: single
(D) TOPOLOGY: linear (vii) IMMEDIATE SOURCE:
(B) CLONE: ZC13006

(xi) SEQUENCE DESCRIPTION: SEQ ID NO:6:

```
GGCTGTCCTC TAAGCGTCAC                                                 20
```

(2) INFORMATION FOR SEQ ID NO:7:

```
    (i) SEQUENCE CHARACTERISTICS:
        (A) LENGTH: 19 base pairs
        (B) TYPE: nucleic acid
        (C) STRANDEDNESS: single
        (D) TOPOLOGY: linear (vii) IMMEDIATE SOURCE:
        (B) CLONE: ZC13007

(xi) SEQUENCE DESCRIPTION: SEQ ID NO:7:

AGGGGTCACA GGGATGCCA                                                 19

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (vii) IMMEDIATE SOURCE:
        (B) CLONE: ZC13809

(xi) SEQUENCE DESCRIPTION: SEQ ID NO:8:

TCGTAGAGAA TTCATGAGTG CGGTATTACT G                                   31

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (vii) IMMEDIATE SOURCE:
        (B) CLONE: ZC13812

(xi) SEQUENCE DESCRIPTION: SEQ ID NO:9:

GGCACCTCAA TGATCCTGGG TCAGC                                          25

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (vii) IMMEDIATE SOURCE:
        (B) CLONE: ZC13804

(xi) SEQUENCE DESCRIPTION: SEQ ID NO:10:

GCTGACCCAG GATCATTGAG GTGCC                                          25

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (vii) IMMEDIATE SOURCE:
        (B) CLONE: ZC13815

(xi) SEQUENCE DESCRIPTION: SEQ ID NO:11:

TGAGCTGGAT CCGCAGGAAG GGCAAACCA                                      29

(2) INFORMATION FOR SEQ ID NO:12:
```

(i) SEQUENCE CHARACTERISTICS:
                  (A) LENGTH: 28 base pairs
                  (B) TYPE: nucleic acid
                  (C) STRANDEDNESS: single
                  (D) TOPOLOGY: linear (vii) IMMEDIATE SOURCE:
                  (B) CLONE: ZC13811

(xi) SEQUENCE DESCRIPTION: SEQ ID NO:12:

AGCTCAGGAT CCCTCCCAGG AGTGCAGG                                                  28

(2) INFORMATION FOR SEQ ID NO:13:

(i) SEQUENCE CHARACTERISTICS:
                  (A) LENGTH: 30 base pairs
                  (B) TYPE: nucleic acid
                  (C) STRANDEDNESS: single
                  (D) TOPOLOGY: linear (vii) IMMEDIATE SOURCE:
                  (B) CLONE: ZC13810

(xi) SEQUENCE DESCRIPTION: SEQ ID NO:13:

TGAGCTTCTA GATTAGCAGG AAGGGCAAAC                                                30

(2) INFORMATION FOR SEQ ID NO:14:

(i) SEQUENCE CHARACTERISTICS:
                  (A) LENGTH: 33 base pairs
                  (B) TYPE: nucleic acid
                  (C) STRANDEDNESS: single
                  (D) TOPOLOGY: linear (vii) IMMEDIATE SOURCE:
                  (B) CLONE: ZC13814

(xi) SEQUENCE DESCRIPTION: SEQ ID NO:14:

AGAGCTGGAT CCCTCACGAG CAGAGAAGAT CCC                                            33

(2) INFORMATION FOR SEQ ID NO:15:

(i) SEQUENCE CHARACTERISTICS:
                  (A) LENGTH: 34 base pairs
                  (B) TYPE: nucleic acid
                  (C) STRANDEDNESS: single
                  (D) TOPOLOGY: linear (vii) IMMEDIATE SOURCE:
                  (B) CLONE: ZC13813

(xi) SEQUENCE DESCRIPTION: SEQ ID NO:15:

AGAGCTTCTA GATTACTCAC GAGCAGAGAA GATC                                           34